(12) United States Patent
Keillor et al.

(10) Patent No.: US 10,591,485 B2
(45) Date of Patent: Mar. 17, 2020

(54) PEPTIDE TAGS FOR FLUORESCENT LABELLING OF PROTEINS

(71) Applicant: UNIVERSITY OF OTTAWA, Ottawa (CA)

(72) Inventors: Jeffrey Keillor, Ottawa (CA); Miroslava Strmiskova, Ottawa (CA)

(73) Assignee: UNIVERSITY OF OTTAWA, Ottawa (CA)

( * ) Notice: Subject to any disclaimer, the term of this patent is extended or adjusted under 35 U.S.C. 154(b) by 230 days.

(21) Appl. No.: 15/004,264

(22) Filed: Jan. 22, 2016

(65) Prior Publication Data

US 2016/0282356 A1  Sep. 29, 2016

Related U.S. Application Data

(60) Provisional application No. 62/106,881, filed on Jan. 23, 2015.

(51) Int. Cl.
*G01N 33/58* (2006.01)
*C07K 14/00* (2006.01)

(52) U.S. Cl.
CPC .......... *G01N 33/582* (2013.01); *C07K 14/00* (2013.01); *C07K 14/001* (2013.01)

(58) Field of Classification Search
CPC ..... C07K 14/00; C07K 14/001; G01N 33/582
See application file for complete search history.

(56) References Cited

U.S. PATENT DOCUMENTS

| | | | |
|---|---|---|---|
| 7,700,375 | B2 | 4/2010 | Keillor et al. |
| 8,835,641 | B2 | 9/2014 | Keillor et al. |
| 9,006,459 | B2 | 4/2015 | Keillor et al. |
| 9,701,667 | B2 | 7/2017 | Keillor et al. |
| 2004/0171014 | A1 | 9/2004 | Smith |
| 2006/0147948 | A1 | 7/2006 | Keillor et al. |
| 2010/0316643 | A1* | 12/2010 | Eckert .................. A01N 37/46 424/134.1 |

OTHER PUBLICATIONS

Chem Pages (Biomolecules Protein 1, p. 4, Acidic and Basic Amino acids, published online 2002).*
Caron, Karine et al., "Dramatic Increase of Quench Efficiency in "Spacerless" Dimaleimide Fluorogens", Organic & Biomolecular Chemistry, 2011, vol. 9, pp. 185-197.
Chen, Yingche et al., "Coumarin-Based Fluorogenic Probes for No-Wash Protein Labeling", Angewandte Chemie International Edition, 2014, vol. 53, pp. 13785-13788.
Girouard, Stéphane et al., "Synthesis and Characterization of Dimaleimide Fluorogens Designed for Specific Labeling of Proteins", J. Am. Chem. Soc., 2005, vol. 127, pp. 559-566.
Guy, Julia et al., "Convergent Preparation and Photophysical Characterization of Dimaleimide Dansyl Fluorogens: Elucidation of the Maleimide Fluorescence Quenching Mechanism", J. Am. Chem. Soc., 2007, vol. 129, pp. 11969-11977.
Guy, Julia et al., "De Novo Helical Peptides as Target Sequences for a Specific, Fluorogenic Protein Labelling Strategy", Molecular Biosystems, 2010, vol. 6, pp. 976-987.
Honda, Kazumasa et al., "Evaluation of Fluorescent Compounds for Peroxyoxalate Chemiluminescence Detection", Analytica Chimica Acta, 1985, vol. 177, pp. 111-120.
Kanaoka, Yuichi et al., "Studies on Protein-Sulfhydryl Reagents. I. Synthesis of Benzimidazole Derivatives of Maleimide; Fluorescent Labeling of Maleimide", Chemical & Pharmaceutical Bulletin, 1964, vol. 12, No. 2, pp. 127-134.
Kellner, Stefanie et al., "Structure-Function Relationship of Substituted Bromomethylcoumarins in Nucleoside Specificity of RNA Alkylation", PLOS ONE, 2013, vol. 8, Issue 7, pp. 1-10.
Langmuir, Margaret et al., "New Naphthopyranone Based Fluorescent Thiol Probes", Tetrahedron Letters, 1995, vol. 36, No. 23, pp. 3989-3992.
Meimetis, Labros G. et al., "Ultrafluorogenic Coumarin-Tetrazine Probes for Real-Time Biological Imaging", Angewandte Chemie International Edition, 2014, vol. 53, pp. 7531-7534.
Liang, F. et al. "Gene index analysis of the human genome estimates approximately 120,000." Nat. Genet. 2000, 25, 239-240.
Roest Crollius, H. et al. "Estimate of human gene number provided by genome-wide analysis using." Nat. Genet. 2000, 25, 235-238.
Ewing, B. et al. "Analysis of expressed sequence tags indicates 35,000 human genes." Nat. Genet. 2000, 25, 232-234.
Haughland, R. P. "Handbook of Fluorescent Probes and Research Chemicals." Molecular Probes. Eugene. Oreg. 1992, 5th Edn.
Sipple, T. O. "New fluorochromes for thiols: maleimide and iodoacetamide derivatives of 3-phenyl coumarin fluorophore." J. Histochem. Cytochem. 1981, 29, 314-316.
Corrie, J. E. T. "Thiol-reactive Fluorescent Probes for Protein Labelling." J. Chem. Soc. Perkin Trans. 1, 1994, 2975-2982.
Zhang, J. et al. "Creating New Fluorescent Probes for Cell Biology." Nature Rev. 2002, 3, 906-918.
Tsien, R. Y. "The Green Fluorescent Protein." Annu. Rev. Biochem. 1998, 67, 509-544.
Griffin, B. A. et al. "Specific Covalent Labeling of Recombinant Protein Molecules Inside Live Cells." Science 1998, 281, 269-272.
Griffin, B. A. et al. "Fluorescent labeling of recombinant proteins in living cells with FlAsH." Methods Enzymol. 2000, 327, 565-578.
Gaietta, G. et al. "Multicolor and Electron Microscopic Imaging of Connexin Trafficking." Science 2002, 296, 503-507.
Girouard, S. et al. "Elaboration d'un fluorophore permettant une étude d'apposition protéique." M. Sc. Thesis. Université de Montréal. 2000.
Houle, M. H. et al. "Synthèse d'un composé fluorogénique permettant l'étude de l'apposition protéique." M. Sc. Thesis. Université de Montréal. 2003.
Yang, J. R. et al. "Synthesis and Properties of a Maleimide Fluorescent Thiol Reagent Derived a Naphtopyranone." J. Heterocyclic Chem. 1991, 28, 1177.
Russo, A. et al. "Detection and quantitation of biological sulfhydryls." Methods Biochem. Anal. 1988, 33, 165-241.
Pace et al., A helix propensity scale based on experimental studies of peptides and protein, , J.M., Biophys. J., 1998, vol. 75, pp. 422-427.

* cited by examiner

*Primary Examiner* — Rachael E Bredefeld
*Assistant Examiner* — Erinne R Dabkowski
(74) *Attorney, Agent, or Firm* — BCF LLP

(57) ABSTRACT

There are provided dicysteine peptide tags for use with dimaleimide fluorescent labelling agents for the labelling and detection of specific protein targets. Peptide tags comprising the amino acid sequence set forth in SEQ ID NO: 2 are described.

$L_1SX_3AECAAX_9EAACREX_{16}X_{17}ARAGGK_{23}$  (SEQ ID NO: 2)

21 Claims, 14 Drawing Sheets

Specification includes a Sequence Listing.

PEPTIDE TAGS FOR FLUORESCENT LABELLING OF PROTEINS

RELATED APPLICATIONS

This application claims priority to U.S. Provisional Application No. 62/106,881 filed on Jan. 23, 2015.

FIELD

The present disclosure relates to peptide tags for the fluorescent labelling and detection of specific protein targets.

BACKGROUND

Fluorescent labelling of a specific protein of interest (POI) is one of the most widely used methods for studying expression, localization and trafficking of proteins inside living cells. Several labelling techniques have been developed that involve, for example, the use of fluorescent dyes bearing reactive functional groups such as succinimidyl esters or maleimides, known to react with amines or thiols (see, for example, Takaoka, Y. et al., Angew. Chem. Int. Ed. 2013, 52 (15), 4088-4106). However these techniques are typically non-specific, as many such functional groups exposed on the surface of any protein may be labelled, and they do not provide a general means for gathering information on specific protein targets.

Several fluorescent probes for imaging in cell biology have been developed, including small organic dyes, quantum dots, intrinsically fluorescent proteins, small genetically encoded tags that can be complexed with fluorochromes, and combinations of these probes (Giepmans, B. N. et al., Science 2006, 312, 217-24). The most widely applied methods for specific protein labelling include the following: 1) fluorescent protein fusion; 2) small-molecule labelling using protein targeting sequences; 3) enzyme substrate fusion; 4) small-molecule labelling using unnatural amino acids; and 5) small-molecule labelling using peptide targeting sequences. For example, in the first of these methods, an intrinsically fluorescent protein (FP) such as the *Aequorea victoria* green fluorescent protein (GFP) is genetically fused to a protein of interest (POI). However, there are limitations to this method, including GFP's slow folding, tendency to aggregate, and its steric bulk, all of which can perturb the native biology of a protein of interest. Other methods currently in use all share similar limitations, such as background labelling of native proteins, perturbation of the native biology of a labelled protein of interest, aggregation, attenuation of the fluorescent signal, toxicity, and/or incompatibility for intracellular labelling.

Recently, techniques have been developed to overcome some of the limitations of existing methods through genetic modification of the target protein and subsequent labelling using small molecules. For example, specific amino acids may be introduced into a POI by mutagenesis, or a peptide or protein tag can be fused to the POI's C- or N-terminus, thereby allowing it to react specifically in a covalent or non-covalent manner with a small molecule.

Maleimides are known to react highly selectively with thiols, and have been used especially for labelling peptide thiols. They are also known to be able to quench fluorescence in their conjugated form. At the same time, cysteines are relatively under-represented amino acid residues in naturally occurring proteins, and are often present only in active sites or in tertiary structural motifs as disulfide bonds. Based on these facts, we developed a non-enzymatic small-molecule labelling method, based on the spontaneous, uncatalyzed Fluorogenic Addition Reaction (FlARe) between a fluorogenic labelling agent and a peptide fusion tag. In these methods, as reported previously, a reactive unit bearing two maleimide groups is linked to a fluorophore, such that fluorescence is quenched by photoinduced electron transfer (PET) until both maleimide groups undergo specific thiol addition reactions (see, e.g., U.S. Pat. No. 7,700,375; U.S. Pat. No. 8,835,641; U.S. Patent Application Publication No. 2015-0316557; Caron, K. et al., Org. Biomol. Chem. 9, 185-197, 2011; Guy, J. et al., Mol. Biosyst. 6: 976-987, 2010; Keillor, J. W. et al., J. Am. Chem. Soc. 129, 11969-11977, 2007; Girouard, S. et al., J. Am. Chem. Soc. 127, 559-566, 2005).

A complementary alpha-helical peptide tag was also designed for use in FlARe labelling methods. Specifically, we synthesized a dicysteine peptide tag bearing two cysteine residues whose thiol side chains are appropriately positioned to react specifically with the two maleimide groups of a fluorogenic molecule comprising a dimaleimide moiety and a fluorophore (U.S. Pat. No. 8,835,641; Guy, J. et al., Mol Biosyst 2010, 6, 976-987). This dicysteine tag (referred to as dC10, for a di-Cysteine alpha-helix with an inter-Cys distance of ~10 Å) was designed to include salt bridges that lock the peptide in a helical conformation and ensure aqueous solubility, as well as a C-cap and an N-cap that confer stability to the small helix by preserving its dipole. Further, the two cysteine residues in the dC10 peptide were separated by two turns of the alpha-helix, and therefore by ~10 Å, to complement fluorogen molecules whose reactive maleimide moieties are also ~10 Å apart.

Genetically fusing these helical peptides to test proteins of interest (POI), we were able to selectively label the target sequence. However, although the dC10 tag has proven useful, the labelling methods are limited by the reactivity and selectivity of the peptide tag.

There is a need therefore for improved peptide tags that are more reactive and/or selective for use in FlARe fluorescent labelling methods.

SUMMARY

It is an object of the present invention to ameliorate at least some of the deficiencies present in the prior art. Embodiments of the present technology have been developed based on the inventors' appreciation that there is a need for improved peptide tags for use with fluorogenic compounds in labelling proteins of interest (POIs).

The present disclosure relates broadly to novel dicysteine peptide tags that are more reactive and/or more selective than known peptides (such as the dC10 peptide) in binding to fluorogenic molecules comprising a dimaleimide moiety and a fluorophore, for use in FlARe labelling techniques.

The present invention is based, at least in part, on the inventor's finding of more reactive dicysteine peptide tags that can offer a kinetic advantage to the labelling reaction, enhancing the selectivity of the FlARe labelling method relative to the background reaction of dimaleimide fluorogens with adventitious thiols such as glutathione. Dicysteine peptide tags provided herein may provide one or more of the following advantages, as compared to the dC10 peptide: faster reaction or higher reactivity with a dimaleimide fluorescent labelling agent; faster visualization and detection of a POI using the FlARe technique; more selective labelling using the FlARe technique, due to reduced background reaction of the dimaleimide fluorescent labelling agent with adventitious cysteine residues; and greater solubility.

In a broad aspect, there is provided herein a dicysteine peptide derived from the dC10 peptide for use in tagging a target protein of interest for fluorescent labelling or detection using a dimaleimide fluorescent labelling agent. In one embodiment, there is provided a peptide comprising the amino acid sequence set forth in SEQ ID NO. 2:

L₁SX₃AECAAX₉EAACREX₁₆X₁₇ARAGGK₂₃   (SEQ ID NO: 2)

wherein:
$X_3$, $X_9$, and $X_{16}$ are independently selected from A, R, K, and H;
and $X_{17}$ is A, D, E, H, K, R, N, Q, or S;
except that when $X_9$ is R or H, at least one of $X_3$, $X_{16}$, and $X_{17}$ is not A,
and when $X_{17}$ is H, either $X_3$ is not A, $X_9$ is not R, or $X_{16}$ is not A; or
a variant, substitution or analog thereof that retains the functional properties of the peptide.

In some embodiments, $X_{17}$ is selected from A, R, K, and H. In an embodiment, $X_3$ is A; $X_9$ is R; $X_{16}$ is A; and $X_{17}$ is D, E, K, R, N, Q, or S. In another embodiment, $X_3$ is A; $X_9$ is R; $X_{16}$ is selected from A, R, K, and H; and $X_{17}$ is A, D, E, H, K, R, N, Q, or S; except that when $X_{17}$ is A or H, $X_{16}$ is not A. In yet another embodiment, $X_3$ is A; $X_{17}$ is A; and $X_9$ and $X_{16}$ are independently selected from A, R, K, and H, except that when $X_9$ is R, $X_{16}$ is not A. In still another embodiment, $X_3$ is A; $X_{16}$ is A; and $X_9$ and $X_{17}$ are independently selected from A, R, K, and H, except that when $X_9$ is R, $X_{17}$ is not A. In another embodiment, $X_9$ is R; $X_{16}$ is A; and $X_3$ and $X_{17}$ are independently selected from A, R, K, and H, except that at least one of $X_3$ and $X_{17}$ is not A. In a further embodiment, $X_9$ is R; $X_{17}$ is A; $X_3$ and $X_{16}$ are independently selected from A, R, K, and H; wherein at least one of $X_3$ and $X_{16}$ is not A. In an embodiment, $X_9$ is R; $X_3$, and $X_{16}$ are independently selected from A, R, K, and H; and $X_{17}$ is A, D, E, H, K, R, N, Q, or S, or $X_{17}$ is selected from A, R, K, and H; wherein at least one of $X_3$, $X_{16}$ and $X_{17}$ is not A, and at least one of $X_3$ and $X_{16}$ is not A when $X_{17}$ is H. In one embodiment, $X_3$ is K; $X_{16}$ is R; and $X_{17}$ is K.

In one embodiment, $X_3$ is not H. In one embodiment, $X_{16}$ is A. In one embodiment, $X_{17}$ is A. In an embodiment, at least one of $X_{16}$ and $X_{17}$ is A.

In an embodiment, there is provided a peptide comprising the amino acid sequence set forth in SEQ ID NO. 3:

L₁SAAECAAREAACREAX₁₇ARAGGK₂₃   (SEQ ID NO: 3)

wherein $X_{17}$ is selected from D, E, K, R, N, Q, and S, or $X_{17}$ is K or R; or
a variant, substitution or analog thereof that retains the functional properties of the peptide.

In an embodiment, there is provided a peptide comprising the amino acid sequence set forth in any one of SEQ ID NOs: 4, 5, 7-18, 23-43, and 60-114, or a variant, substitution or analog thereof that retains the functional properties of the peptide.

In some embodiments, there is provided a peptide consisting of the amino acid sequence set forth in any one of SEQ ID NOs: 2-4, 5, 7-18, 23-43, and 60-114, or a variant, substitution or analog thereof that retains the functional properties of the peptide.

In some embodiments, a peptide provided herein binds specifically to a dimaleimide fluorescent labelling agent. In a particular embodiment, a peptide reacts faster with a dimaleimide fluorescent labelling agent than the dC10 peptide, e.g., the peptide reacts at least about 1.5× faster, at least about 2.5× faster, at least about 5× faster, or about 10× faster with a dimaleimide fluorescent labelling agent than the dC10 peptide.

A peptide may be synthetic, isolated, purified, or substantially pure.

In some embodiments, there is provided a variant, substitution, or analog of a peptide provided herein, wherein the variant, substitution or analog retains the functional properties of the peptide, e.g., retains the binding properties of the peptide to a dimaleimide fluorescent labelling agent. In an embodiment, a variant, substitution, or analog comprises one or more amino acid substitution at position 1, 2, 3, 4, 5, 7, 8, 9, 10, 11, 12, 14, 15, 16, 17, 18, 19, 20, 21, 22, or 23 of the peptide. In another embodiment, a variant substitution, or analog reacts at least about 1.5× faster, at least about 2.5× faster, at least about 5× faster, or about 10× faster with a dimaleimide fluorescent labelling agent than the dC10 peptide.

In some embodiments, the dimaleimide fluorescent labelling agent is

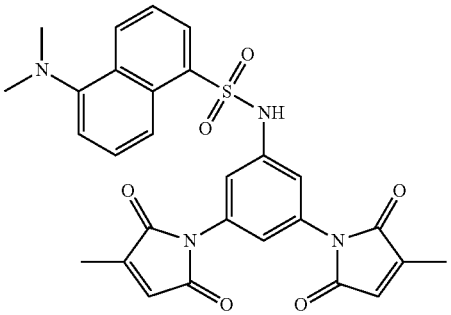

1

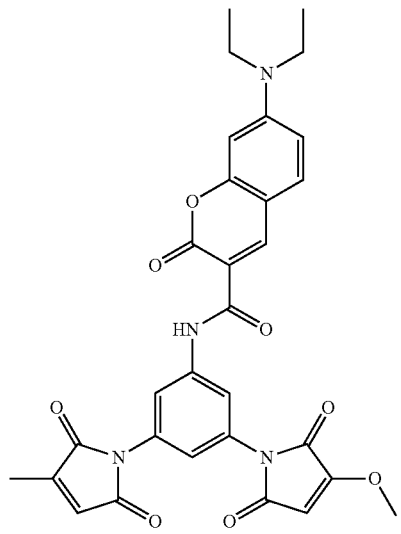

2

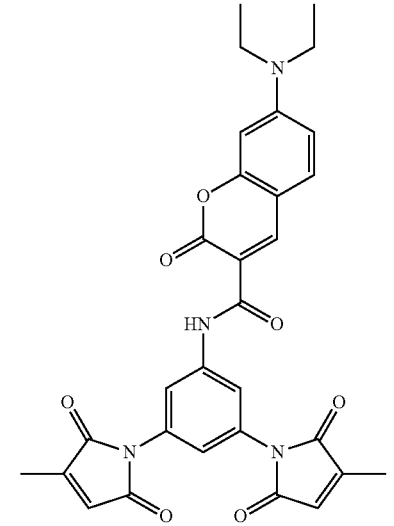

3

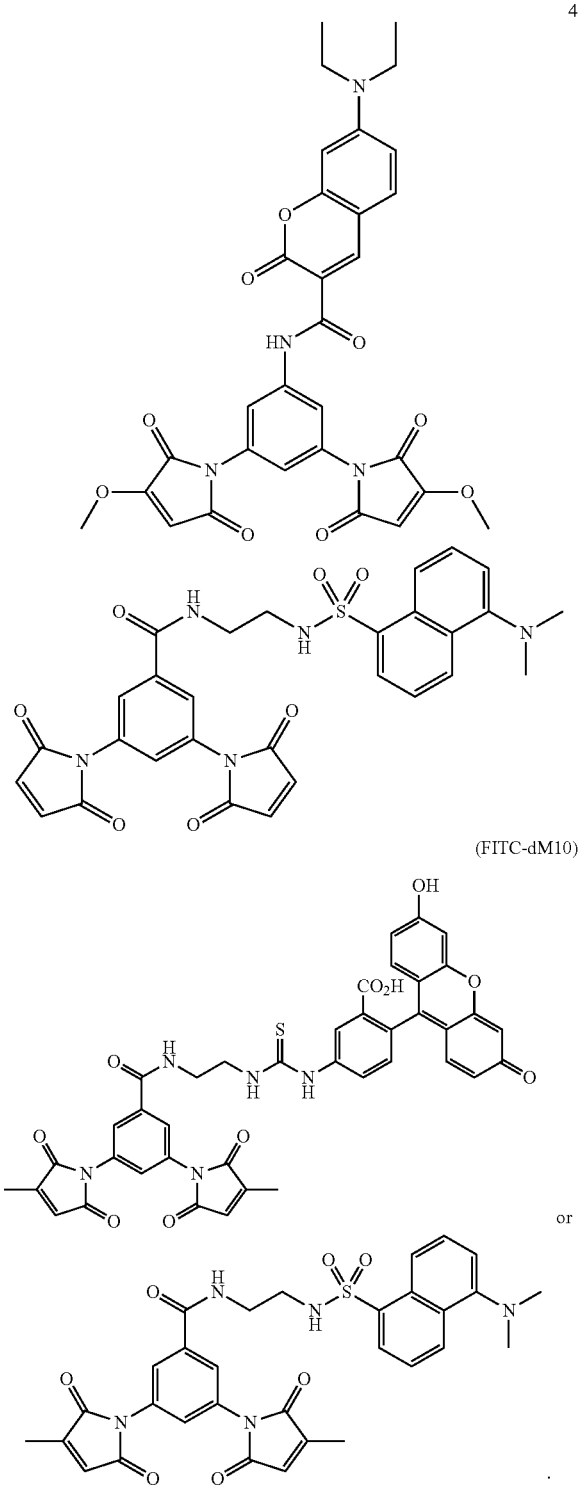

(FITC-dM10)

In some embodiments, a peptide of the invention is provided in the form of a fusion product (e.g., a fusion protein) in which the peptide is linked to a target protein of interest.

In another aspect, there is provided an isolated or recombinant nucleic acid encoding the peptide (or fusion product) of the invention. A nucleic acid may be, e.g., DNA or RNA. In some embodiments, a nucleic acid is provided in a vector, such as an expression vector for producing the peptide (or fusion product) in a cell, or a vector for incorporating the nucleic acid into the genomic DNA of a cell, or a cloning vector for propagating the nucleic acid in a cell. Thus, there are also provided vectors and other recombinant constructs comprising the nucleic acid encoding the peptide (or fusion product) of the invention.

In another aspect, there is provided a cell comprising the nucleic acid, vector, peptide, and/or fusion product of the invention. A cell may be a cultured cell or a cell in an organism, e.g., an animal, in which it is desired to visualize a target protein. A cell may also be a host cell into which a nucleic acid or vector is transfected, e.g., in order to produce the peptide (or fusion protein) of the invention. A cell may be, without limitation, a bacterial cell such as an E. coli cell, or an animal cell such as a mammalian cell, an invertebrate cell, a vertebrate cell, a human cell, a rodent cell, a mouse cell, a rat cell, an insect cell, a nematode cell, a yeast cell, or a fish cell.

In yet another aspect, there is provided a method for detecting and/or labelling a target protein, comprising: a) fusing the target protein to a peptide or variant, substitution, or analog thereof of the invention; b) contacting the target protein with a dimaleimide fluorescent labelling agent under conditions where the dimaleimide fluorescent labelling agent reacts with the peptide fused to the target protein, wherein the fluorescence of the dimaleimide fluorescent labelling agent is quenched in the absence of reaction with the target protein; and c) upon reaction of the dimaleimide fluorescent labelling agent with the peptide fused to the target protein, detecting a fluorescent signal from the dimaleimide fluorescent labelling agent. In some embodiments, the peptide is genetically fused to the target protein.

In some embodiments, fluorescence of the dimaleimide fluorescent labelling agent increases after reaction with the target protein or is detectable only after reaction with the target protein.

In embodiments of methods of the invention, the contacting may occur in vivo, ex vivo, or in vitro. In some embodiments, the contacting may occur in a cultured cell expressing a protein of interest (POI) or target protein, e.g., genetically fused to the peptide. In other embodiments, the contacting may occur in a cell expressing a protein of interest (POI) or target protein, e.g., genetically fused to the peptide, in an organism, e.g., in an animal. The target protein may be, for example, an intracellular protein, or an extracellular or cell-surface protein. The contacting may occur intracellularly in some embodiments.

There are also provided herein methods for live imaging of a target protein, as well as for assaying biomolecular interactions between two target molecules, e.g., two target proteins.

In a further aspect, there is provided a kit for labelling and/or detecting a target protein linked to a peptide of the invention. A kit may comprise a nucleic acid, vector, peptide, or fusion product of the invention; optionally, a dimaleimide fluorescent labelling agent; and instructions for use thereof.

BRIEF DESCRIPTION OF THE DRAWINGS

For a better understanding of the invention and to show more clearly how it may be carried into effect, reference will now be made by way of example to the accompanying drawings, which illustrate aspects and features according to embodiments of the present invention, and in which.

DETAILED DESCRIPTION

Figure 1:
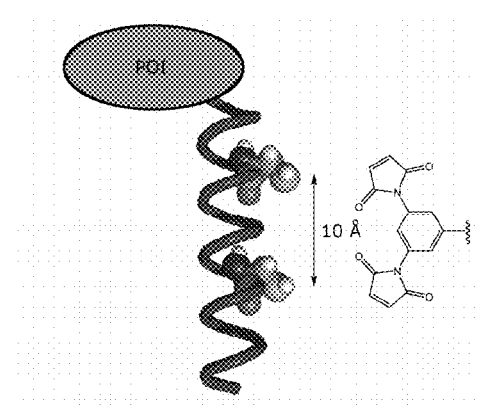
FIG. 1 is a schematic drawing illustrating the design of FlARe labelling components in one embodiment of the invention, in which the dicysteine tag (tag shown in red, sulfur atoms of cysteine residues shown in yellow) linked to a protein of interest (POI) is shown reacting with the dimaleimide moiety of a fluorogen (on the right) with adequate distance of 10 Å between two cysteines and two maleimide groups.
Figure 2:
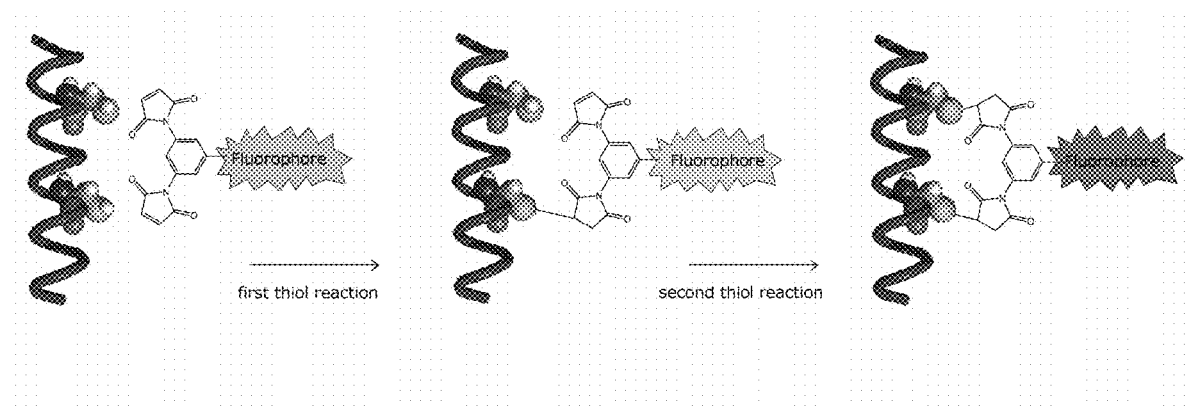
FIG. 2 is a schematic drawing illustrating a fluorogenic addition reaction scheme in one embodiment of the invention, in which addition of a first thiol from a dicysteine peptide produces a slightly fluorescent complex (middle), and fluorescence is completely restored only after a second thiol is added on the dimaleimide fluorogen molecule (right).

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The terms "derivative" and "variant" are used interchangeably herein.

There are provided herein peptides and methods of use thereof for detection and labelling of specific proteins of interest using FlARe techniques. Dicysteine peptides presented herein are designed to be highly reactive and/or selective in binding to dimaleimide fluorescent labelling agents for use in fluorogenic addition reaction (FlARe) labelling methods. The dicysteine peptide sequence presents appropriately spaced, solvent-exposed Cys residues that react with dimaleimide fluorescent labelling agents having a similar spacing between their maleimide groups. Such fluorescent labelling methods can be advantageous in several respects, including high specificity, low background staining, and/or reduced disruption of the localization and interactions of native proteins by the peptide tag as compared to the relatively large protein fragments used in other methods.

We report herein the design and production of derivatives of the previously described dC10 peptide (also referred to herein as the "parent" peptide; see Guy, J. et al., Mol. Biosyst. 6: 976-987, 2010). dC10-derivative peptides provided herein display improved properties, compared to dC10, in FlARe labelling techniques.

For example, peptides provided herein may have one or more of the following advantages: high reactivity with a dimaleimide fluorescent labelling agent; high selectivity of binding to a dimaleimide fluorescent labelling agent; fast reaction or binding with a dimaleimide fluorescent labelling agent, as compared to the parent dC10 peptide; and high solubility, as compared to the parent dC10 peptide. In one embodiment, the peptide provided herein reacts faster with a dimaleimide fluorescent labelling agent than the parent dC10 tag. Without wishing to be bound by theory, it is believed that faster reaction leads to more selective labelling of a tagged protein of interest inside a cell, where a fluorogenic labelling molecule can be exposed to a large number of potentially reactive thiols.

In some embodiments, a peptide of the invention reacts with a dimaleimide fluorescent labelling agent faster than the dC10 peptide, e.g., about 1.5 times (1.5×) faster, about 2.5 times (2.5×) faster, about 5× faster, or about 10× faster. In some embodiments, a peptide of the invention reacts at least about 1.5× faster, at least about 2.5× faster, at least about 5× faster, or at least about 10× faster than the dC10 peptide with a dimaleimide fluorescent labelling agent. The rate of reaction can be determined by measuring, for example, the second order rate constant of the reaction, using standard techniques and as described herein.

In particular embodiments, a peptide reacts faster with a dimaleimide fluorescent labelling agent selected from

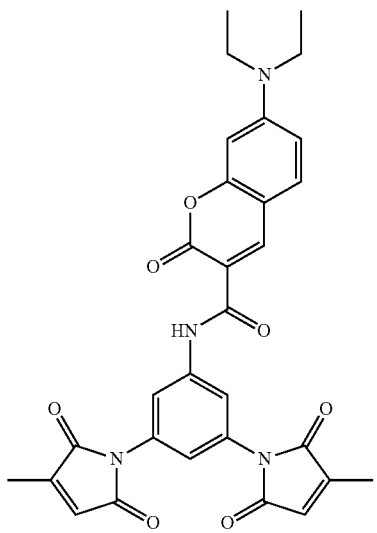

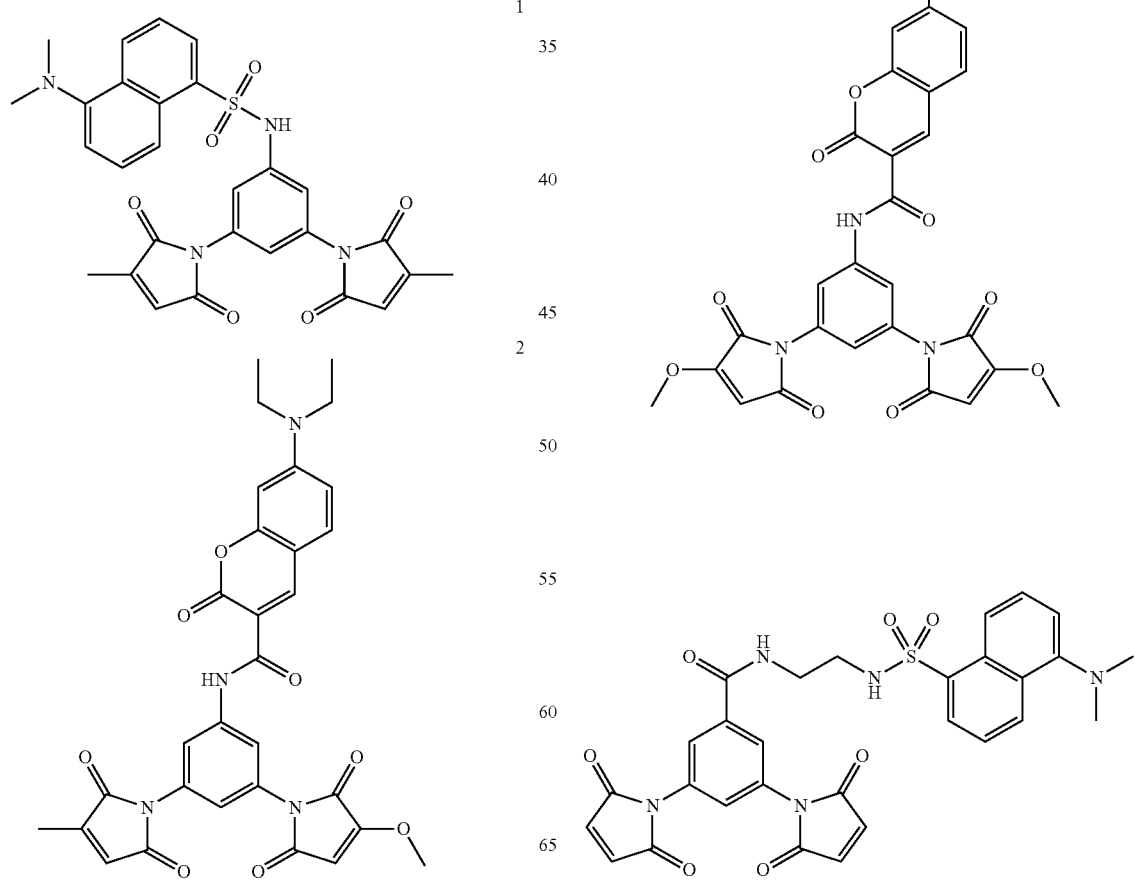

-continued

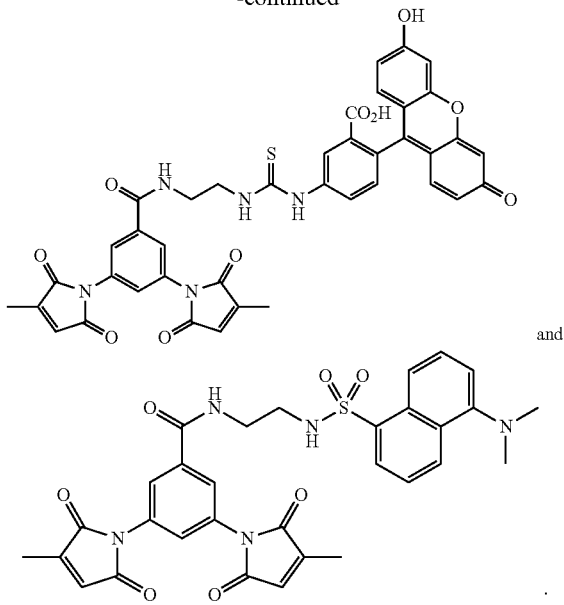

and

In some embodiments, dicysteine peptides provided herein comprise one or more amino acid substitutions in the dC10 peptide (SEQ ID NO: 1). In an embodiment, a peptide comprises an amino acid substitution at one or more of positions 3, 9, 16, and 17 of SEQ ID NO: 1. In another embodiment, a peptide comprises a single amino acid substitution at position 3, 9, 16, or 17 of SEQ ID NO: 1. In another embodiment, a peptide comprises an amino acid substitution at two or more of positions 3, 9, 16, and 17 of SEQ ID NO: 1. For example, a peptide may comprise an amino acid substitution at positions 3 and 9, 3 and 16, 3 and 17, 16 and 17, 9 and 16, or 9 and 17 of SEQ ID NO: 1. In another embodiment, a peptide comprises an amino acid substitution at three or more of positions 3, 9, 16, and 17 of SEQ ID NO: 1. For example, in an embodiment a peptide comprises an amino acid substitution at positions 3, 16, and 17, or at positions 9, 16, and 17 of SEQ ID NO: 1. In some embodiments, the parent amino acids at these positions are substituted by K, R, or H.

In one embodiment, there is provided a peptide comprising the amino acid sequence set forth in SEQ ID NO: 2:

$L_1SX_3AECAAX_9EAACREX_{16}X_{17}ARAGGK_{23}$ (SEQ ID NO: 2)

wherein:

$X_3$, $X_9$, and $X_{16}$ are independently selected from A, R, K, and H; and $X_{17}$ is A, D, E, H, K, R, N, Q, or S;

except that when $X_9$ is R or H, at least one of $X_3$, $X_{16}$, and $X_{17}$ is not A, and when $X_{17}$ is H, either $X_3$ is not A, $X_9$ is not R, or $X_{16}$ is not A.

In an embodiment, $X_{17}$ is selected from A, R, K, and H.

In another embodiment, $X_3$ is A; $X_9$ is R; $X_{16}$ is A; and $X_{17}$ is D, E, K, R, N, Q, or S.

In yet another embodiment, $X_3$ is A; $X_9$ is R; $X_{16}$ is selected from A, R, K, and H; and $X_{17}$ is A, D, E, H, K, R, N, Q, or S; except that when $X_{17}$ is A or H, $X_{16}$ is not A.

In still another embodiment, $X_3$ is A; $X_{17}$ is A; and $X_9$ and $X_{16}$ are independently selected from A, R, K, and H, except that when $X_9$ is R, $X_{16}$ is not A.

In another embodiment, $X_3$ is A; $X_{16}$ is A; and $X_9$ and $X_{17}$ are independently selected from A, R, K, and H, except that when $X_9$ is R, $X_{17}$ is not A.

In a further embodiment, $X_9$ is R; $X_{16}$ is A; and $X_3$ and $X_{17}$ are independently selected from A, R, K, and H, except that at least one of $X_3$ and $X_{17}$ is not A.

In another embodiment, $X_9$ is R; $X_{17}$ is A; and $X_3$ and $X_{16}$ are independently selected from A, R, K, and H; wherein at least one of $X_3$ and $X_{16}$ is not A.

In another embodiment, $X_9$ is R; $X_3$ and $X_{16}$ are independently selected from A, R, K, and H; and $X_{17}$ is A, D, E, H, K, R, N, Q, or S; wherein at least one of $X_3$, $X_{16}$ and $X_{17}$ is not A. In an embodiment, $X_9$ is R; $X_3$ and $X_{16}$ are independently selected from A, R, K, and H; and $X_{17}$ is selected from A, R, K, and H.

In one embodiment, $X_3$ is K; $X_9$ is R; $X_{16}$ is R; and $X_{17}$ is K.

In one embodiment, $X_3$ is not H.

In one embodiment, $X_{16}$ is A. In one embodiment, $X_{17}$ is A. In an embodiment, at least one of $X_{16}$ and $X_{17}$ is A.

In another embodiment, there is provided a peptide comprising the amino acid sequence set forth in SEQ ID NO: 3:

$L_1SAAECAAREAACREAX_{17}ARAGGK_{23}$ (SEQ ID NO: 3)

wherein $X_{17}$ is selected from D, E, K, R, N, Q, and S. In an embodiment, $X_{17}$ is K or R.

In an embodiment, there is provided a peptide comprising the amino acid sequence set forth in any one of SEQ ID NOs: 4, 5, 7-18, 23-43, and 60-114.

In an embodiment, there is provided a peptide consisting of the amino acid sequence set forth in SEQ ID NO: 2:

$L_1SX_3AECAAX_9EAACREX_{16}X_{17}ARAGGK_{23}$ (SEQ ID NO: 2)

wherein $X_3$, $X_9$, $X_{16}$ and $X_{17}$ are as defined above.

In another embodiment, there is provided a peptide consisting of the amino acid sequence set forth in SEQ ID NO: 3:

$L_1SAAECAAREAACREAX_{17}ARAGGK_{23}$ (SEQ ID NO: 3)

wherein $X_{17}$ is selected from D, E, K, R, N, Q, and S. In an embodiment, $X_{17}$ is K or R.

In one embodiment, there is provided a peptide consisting of the amino acid sequence set forth in any one of SEQ ID NOs: 4, 5, 7-18, and 23-43.

In some embodiments, dicysteine peptides provided herein comprise a peptide having the sequence set forth in SEQ ID NO: 60 (referred to herein as the "dC15" peptide). In the dC15 peptide, the first cysteine residue is placed at position 7 instead of position 6 in the peptide.

Dicysteine peptides provided herein may also comprise one or more amino acid substitutions in the dC15 peptide. In an embodiment, a peptide comprises an amino acid substitution at one or more of positions 3, 4, and 11 of SEQ ID NO: 60. In another embodiment, a peptide comprises a single amino acid substitution (e.g., H, R, or K) at position 3, 4, or 11 of SEQ ID NO: 60. In another embodiment, a peptide comprises an amino acid substitution (e.g., H, R, or K) at two or more of positions 3, 4, and 11 of SEQ ID NO: 60. For example, a peptide may comprise an amino acid substitution at positions 3 and 4, 3 and 11, or 4 and 11 of SEQ ID NO: 60. In another embodiment, a peptide comprises an amino acid substitution at each of positions 3, 4, and 11 of SEQ ID NO: 60. In some embodiments, the parent amino acids at these positions are substituted by K, R, or H. In one embodiment, there is provided a peptide consisting of the amino acid sequence set forth in any one of SEQ ID NOs: 60-114.

The amino acid sequence of the parent dC10 peptide and exemplary derivatives thereof are given in Table 1.

TABLE 1

Exemplary dicysteine peptides.

| Name | Amino acid sequence | SEQ ID NO. |
|---|---|---|
| dC10 | $L_1$SAAECAAREAACREAAARAGGK$_{23}$ | 1 |
| dC10-A3X$_3$R9X$_9$A16X$_{16}$A17X$_{17}$ | $L_1$SX$_3$AECAAX$_9$EAACREX$_{16}$X$_{17}$ARAGGK$_{23}$ | 2 |
| dC10-A17X$_{17}$ | $L_1$SAAECAAREAACREAX$_{17}$ARAGGK$_{23}$ | 3 |
| dC10-A17D | $L_1$SAAECAAREAACREADARAGGK$_{23}$ | 4 |
| dC10-A17E | $L_1$SAAECAAREAACREAEARAGGK$_{23}$ | 5 |
| dC10-A17H | $L_1$SAAECAAREAACREAHARAGGK$_{23}$ | 6 |
| dC10-A17K | $L_1$SAAECAAREAACREAKARAGGK$_{23}$ | 7 |
| dC10-A17N | $L_1$SAAECAAREAACREANARAGGK$_{23}$ | 8 |
| dC10-A17Q | $L_1$SAAECAAREAACREAQARAGGK$_{23}$ | 9 |
| dC10-A17R | $L_1$SAAECAAREAACREARARAGGK$_{23}$ | 10 |
| dC10-A17S | $L_1$SAAECAAREAACREASARAGGK$_{23}$ | 11 |
| dC10-A16K | $L_1$SAAECAAREAACREKAARAGGK$_{23}$ | 12 |
| dC10-A16R | $L_1$SAAECAAREAACRERAARAGGK$_{23}$ | 13 |
| dC10-A16H | $L_1$SAAECAAREAACREHAARAGGK$_{23}$ | 14 |
| dC10-A3K | $L_1$SKAECAAREAACREAAARAGGK$_{23}$ | 15 |
| dC10-A3R | $L_1$SRAECAAREAACREAAARAGGK$_{23}$ | 16 |
| dC10-A3H | $L_1$SHAECAAREAACREAAARAGGK$_{23}$ | 17 |
| dC10-R9K | $L_1$SAAECAAKEAACREAAARAGGK$_{23}$ | 18 |
| dC10-S2H | $L_1$HAAECAAREAACREAAARAGGK$_{23}$ | 19 |
| dC10-A7H | $L_1$SAAECHAREAACREAAARAGGK$_{23}$ | 20 |
| dC10-R9H | $L_1$SAAECAAHEAACREAAARAGGK$_{23}$ | 21 |
| dC10-S2HA17H | $L_1$HAAECAAREAACREAHARAGGK$_{23}$ | 22 |
| dC10-R9KA17H | $L_1$SAAECAAKEAACREAHARAGGK$_{23}$ | 23 |
| dC10-R9KA17K | $L_1$SAAECAAKEAACREAKARAGGK$_{23}$ | 24 |
| dC10-R9KA17R | $L_1$SAAECAAKEAACREARARAGGK$_{23}$ | 25 |
| dC10-R9HA17H | $L_1$SAAECAAHEAACREAHARAGGK$_{23}$ | 26 |
| dC10-R9HA17K | $L_1$SAAECAAHEAACREAKARAGGK$_{23}$ | 27 |
| dC10-R9HA17R | $L_1$SAAECAAHEAACREARARAGGK$_{23}$ | 28 |
| dC10-R9KA16H | $L_1$SAAECAAKEAACREHAARAGGK$_{23}$ | 29 |
| dC10-R9KA16K | $L_1$SAAECAAKEAACREKAARAGGK$_{23}$ | 30 |
| dC10-R9KA16R | $L_1$SAAECAAKEAACRERAARAGGK$_{23}$ | 31 |
| dC10-A16HA17K | $L_1$SAAECAAREAACREHKARAGGK$_{23}$ | 32 |
| dC10-A16KA17K | $L_1$SAAECAAREAACREKKARAGGK$_{23}$ | 33 |
| dC10-A16RA17K | $L_1$SAAECAAREAACRERKARAGGK$_{23}$ | 34 |
| dC10-A3HA16HA17K | $L_1$SHAECAAREAACREHKARAGGK$_{23}$ | 35 |
| dC10-A3KA16HA17K | $L_1$SKAECAAREAACREHKARAGGK$_{23}$ | 36 |
| dC10-A3RA16HA17K | $L_1$SRAECAAREAACREHKARAGGK$_{23}$ | 37 |
| dC10-A3HA16KA17K | $L_1$SHAECAAREAACREKKARAGGK$_{23}$ | 38 |
| dC10-A3KA16KA17K | $L_1$SKAECAAREAACREKKARAGGK$_{23}$ | 39 |
| dC10-A3RA16KA17K | $L_1$SRAECAAREAACREKKARAGGK$_{23}$ | 40 |
| dC10-A3HA16RA17K | $L_1$SHAECAAREAACRERKARAGGK$_{23}$ | 41 |
| dC10-A3KA16RA17K (also called dC10*) | $L_1$SKAECAAREAACRERKARAGGK$_{23}$ | 42 |
| dC10-A3RA16RA17K | $L_1$SRAECAAREAACRERKARAGGK$_{23}$ | 43 |
| dC15 | $L_1$SAAEAC$_7$AREAAAREAAC$_{18}$RAGGK$_{23}$ | 60 |
| dC15-A11H | $L_1$SAAEAC$_7$AREHAAREAAC$_{18}$RAGGK$_{23}$ | 61 |
| dC15-A11R | $L_1$SAAEAC$_7$ARERAAREAAC$_{18}$RAGGK$_{23}$ | 62 |
| dC15-A11K | $L_1$SAAEAC$_7$AREKAAREAAC$_{18}$RAGGK$_{23}$ | 63 |
| dC15-A4H | $L_1$SAHEAC$_7$AREAAAREAAC$_{18}$RAGGK$_{23}$ | 64 |
| dC15-A4R | $L_1$SAREAC$_7$AREAAAREAAC$_{18}$RAGGK$_{23}$ | 65 |
| dC15-A4K | $L_1$SAKEAC$_7$AREAAAREAAC$_{18}$RAGGK$_{23}$ | 66 |
| dC15-A3H | $L_1$SHAEAC$_7$AREAAAREAAC$_{18}$RAGGK$_{23}$ | 67 |
| dC15-A3R | $L_1$SRAEAC$_7$AREAAAREAAC$_{18}$RAGGK$_{23}$ | 68 |
| dC15-A3K | $L_1$SKAEAC$_7$AREAAAREAAC$_{18}$RAGGK$_{23}$ | 69 |
| dC15-A4HA11H | $L_1$SAHEAC$_7$AREHAAREAAC$_{18}$RAGGK$_{23}$ | 70 |
| dC15-A4RA11H | $L_1$SAREAC$_7$AREHAAREAAC$_{18}$RAGGK$_{23}$ | 71 |
| dC15-A4KA11H | $L_1$SAKEAC$_7$AREHAAREAAC$_{18}$RAGGK$_{23}$ | 72 |
| dC15-A4HA11R | $L_1$SAHEAC$_7$ARERAAREAAC$_{18}$RAGGK$_{23}$ | 73 |
| dC15-A4RA11R | $L_1$SAREAC$_7$ARERAAREAAC$_{18}$RAGGK$_{23}$ | 74 |
| dC15-A4KA11R | $L_1$SAKEAC$_7$ARERAAREAAC$_{18}$RAGGK$_{23}$ | 75 |
| dC15-A4HA11R | $L_1$SAHEAC$_7$AREKAAREAAC$_{18}$RAGGK$_{23}$ | 76 |
| dC15-A4RA11R | $L_1$SAREAC$_7$AREKAAREAAC$_{18}$RAGGK$_{23}$ | 77 |
| dC15-A4KA11R | $L_1$SAKEAC$_7$AREKAAREAAC$_{18}$RAGGK$_{23}$ | 78 |
| dC15-A3HA11H | $L_1$SHAEAC$_7$AREHAAREAAC$_{18}$RAGGK$_{23}$ | 79 |
| dC15-A3RA11H | $L_1$SRAEAC$_7$AREHAAREAAC$_{18}$RAGGK$_{23}$ | 80 |
| dC15-A3KA11H | $L_1$SKAEAC$_7$AREHAAREAAC$_{18}$RAGGK$_{23}$ | 81 |
| dC15-A3HA11R | $L_1$SHAEAC$_7$ARERAAREAAC$_{18}$RAGGK$_{23}$ | 82 |
| dC15-A3RA11R | $L_1$SRAEAC$_7$ARERAAREAAC$_{18}$RAGGK$_{23}$ | 83 |
| dC15-A3KA11R | $L_1$SKAEAC$_7$ARERAAREAAC$_{18}$RAGGK$_{23}$ | 84 |

TABLE 1-continued

Exemplary dicysteine peptides.

| Name | Amino acid sequence | SEQ ID NO. |
|---|---|---|
| dC15-A3HA11K | $L_1SHAEAC_7AREKAAREAAC_{18}RAGGK_{23}$ | 85 |
| dC15-A3RA11K | $L_1SRAEAC_7AREKAAREAAC_{18}RAGGK_{23}$ | 86 |
| dC15-A3KA11K | $L_1SKAEAC_7AREKAAREAAC_{18}RAGGK_{23}$ | 87 |
| dC15-A3HA4HA11H | $L_1SHHEAC_7AREHAAREAAC_{18}RAGGK_{23}$ | 88 |
| dC15-A3HA4RA11H | $L_1SHREAC_7AREHAAREAAC_{18}RAGGK_{23}$ | 89 |
| dC15-A3HA4KA11H | $L_1SHKEAC_7AREHAAREAAC_{18}RAGGK_{23}$ | 90 |
| dC15-A3HA4HA11R | $L_1SHHEAC_7ARERAAREAAC_{18}RAGGK_{23}$ | 91 |
| dC15-A3HA4RA11R | $L_1SHREAC_7ARERAAREAAC_{18}RAGGK_{23}$ | 92 |
| dC15-A3HA4KA11R | $L_1SHKEAC_7ARERAAREAAC_{18}RAGGK_{23}$ | 93 |
| dC15-A3HA4HA11K | $L_1SHHEAC_7AREKAAREAAC_{18}RAGGK_{23}$ | 94 |
| dC15-A3HA4RA11K | $L_1SHREAC_7AREKAAREAAC_{18}RAGGK_{23}$ | 95 |
| dC15-A3HA4KA11K | $L_1SHKEAC_7AREKAAREAAC_{18}RAGGK_{23}$ | 96 |
| dC15-A3RA4HA11H | $L_1SRHEAC_7AREHAAREAAC_{18}RAGGK_{23}$ | 97 |
| dC15-A3RA4RA11H | $L_1SRREAC_7AREHAAREAAC_{18}RAGGK_{23}$ | 98 |
| dC15-A3RA4KA11H | $L_1SRKEAC_7AREHAAREAAC_{18}RAGGK_{23}$ | 99 |
| dC15-A3RA4HA11R | $L_1SRHEAC_7ARERAAREAAC_{18}RAGGK_{23}$ | 100 |
| dC15-A3RA4RA11R | $L_1SRREAC_7ARERAAREAAC_{18}RAGGK_{23}$ | 101 |
| dC15-A3RA4KA11R | $L_1SRKEAC_7ARERAAREAAC_{18}RAGGK_{23}$ | 102 |
| dC15-A3RA4HA11K | $L_1SRHEAC_7AREKAAREAAC_{18}RAGGK_{23}$ | 103 |
| dC15-A3RA4RA11K | $L_1SRREAC_7AREKAAREAAC_{18}RAGGK_{23}$ | 104 |
| dC15-A3RA4KA11K | $L_1SRKEAC_7AREKAAREAAC_{18}RAGGK_{23}$ | 105 |
| dC15-A3KA4HA11H | $L_1SKHEAC_7AREHAAREAAC_{18}RAGGK_{23}$ | 106 |
| dC15-A3KA4RA11H | $L_1SKREAC_7AREHAAREAAC_{18}RAGGK_{23}$ | 107 |
| dC15-A3KA4KA11H | $L_1SKKEAC_7AREHAAREAAC_{18}RAGGK_{23}$ | 108 |
| dC15-A3KA4HA11R | $L_1SKHEAC_7ARERAAREAAC_{18}RAGGK_{23}$ | 109 |
| dC15-A3KA4RA11R | $L_1SKREAC_7ARERAAREAAC_{18}RAGGK_{23}$ | 110 |
| dC15-A3KA4KA11R | $L_1SKKEAC_7ARERAAREAAC_{18}RAGGK_{23}$ | 111 |
| dC15-A3KA4HA11K | $L_1SKHEAC_7AREKAAREAAC_{18}RAGGK_{23}$ | 112 |
| dC15-A3KA4RA11K | $L_1SKREAC_7AREKAAREAAC_{18}RAGGK_{23}$ | 113 |
| dC15-A3KA4KA11K | $L_1SKKEAC_7AREKAAREAAC_{18}RAGGK_{23}$ | 114 |

In some embodiments, there are provided variants, substitutions, or analogs of the above-described peptides. It should be understood that variants, substitutions, or analogs of peptides provided herein that retain the functional properties of the starting peptide are also encompassed by the present invention. For example, in some cases one or more amino acids in a peptide can be substituted by another amino acid without abrogating the functional properties of the peptide. Non-limiting examples of such functional properties include the peptide's binding properties (reactivity, affinity, and/or selectivity) for binding to a dimaleimide fluorescent labelling agent, and the peptide's solubility. In one embodiment, a variant, substitution, or analog of the above-described peptides retains the ability to react with a dimaleimide fluorescent labelling agent faster than the dC10 peptide, e.g., at least about 1.5× faster, at least about 2.5× faster, at least about 5× faster, or about 10× faster, as determined for example by measuring the rate constant of the reaction.

In an embodiment, a variant, substitution, or analog comprises an amino acid substitution at one or more of positions 1, 2, 3, 4, 5, 7, 8, 9, 10, 11, 12, 14, 15, 16, 17, 18, 19, 20, 21, 22, or 23 of SEQ ID NOs: 2-4, 5, 7-18, 23-43, and 60-114. It will be understood that in some embodiments, a variant, substitution, or analog of the above-described peptides retains the Cys residues at positions 6 and 13 of the peptide, so as not to disrupt the functional properties of the peptide in binding to a dimaleimide fluorescent labelling agent. In some embodiments, a variant, substitution, or analog does not include SEQ ID NOs: 1, 6, or 19-22.

As used herein, a "variant, substitution or analog" refers to modifications or changes in a single amino acid or a small percentage of amino acids (e.g., less than 10%, less than 5%, or less than 1%) in the peptide sequence, such that the functional properties of the peptide are retained. Conservative amino acid substitutions providing functionally similar amino acids are well known in the art and include substitutions of amino acids having substantially the same charge, size, hydrophilicity, and/or aromaticity as the amino acid replaced. Such substitutions, known to those of ordinary skill in the art, include for example glycine-alanine-valine; isoleucine-leucine; tryptophan-tyrosine; aspartic acid-glutamic acid; arginine-lysine; asparagine-glutamine; and serine-threonine. Analogs of naturally occurring amino acids are also known in the art and may be used in peptides of the invention. For example, a peptide may include one or more amino acid derivative or non-natural amino acid such as, without limitation, a D-amino acid; a homo-amino acid (e.g., a β-amino acid); an α-alkyl amino acid; a dehydroamino acid, an α,α-disubstituted amino acid; cystine; 5-hydroxy lysine; 4-hydroxy proline; α-aminoadipic acid; α-amino-ra-butyric acid; 3,4-dihydroxyphenylalanine; homoserine; α-methylserine; ornithine; pipecolic acid; ortho, meta or para-aminobenzoic acid; citrulline; canavanine; norleucine; δ-glutamic acid; aminobutyric acid; L-fluorenylalanine; L-3-benzothienylalanine; and thyroxine. Additional amino acids that may be included in the peptide of the present invention include, without limitation: aminobutyric acid; homophenylalanine; norvaline; arninoisobutyric acid; ethylglycine; butylglycine; penicillamine; I-naphthylalanine; cyclohexylalanine; cyclopentylalanine; aminocyclopropane carboxylate; aminonorbomylcarboxylate; α-methylalarnine; α-methylcysteine; and derivatives thereof.

Generally, two or more amino acid sequences (or two or more nucleotide sequences) are considered to be "substantially identical" or "substantially similar" if the amino acid sequences or the nucleotide sequences share at least 90% sequence identity with each other, or with a reference sequence over a given comparison window. Thus, substantially similar sequences include those having, for example, at least 90% sequence identity, at least 95% sequence identity, at least 97% sequence identity, or at least 99% sequence identity.

In some embodiments, dicysteine peptides provided herein comprise or consist of more than one copy of SEQ ID NOs: 1-43 or 60-114. Two or more copies of the same peptide may be used, for example, two or more peptides of SEQ ID NO: 2 may be linked in tandem. Alternatively, two or more different peptides may be used together, for example a peptide of SEQ ID NO: 1 may be linked to a peptide of SEQ ID NO: 2, or a peptide of SEQ ID NO: 3 may be linked to a peptide of SEQ ID NO: 4, etc.

It should also be understood that a dicysteine peptide provided herein may be provided as part of a longer peptide, e.g., a 15-amino acid peptide, a 20-amino acid peptide, a 25 amino-acid peptide, etc. Thus, additional amino acids may be added at the N- or C-terminal of a dicysteine peptide provided herein, as long as the functional properties of the peptide are retained.

A peptide of the present invention can be produced using a known chemical synthesis method (such as, for example, a liquid phase synthesis method, a solid phase synthesis method, etc.; see, for example, Izumiya, N. et al., "Basis and Experiments of Peptide Synthesis", 1985, Maruzen Co., Ltd.). Thus, in some embodiments a peptide is synthetic.

Alternatively, a peptide can be produced by expression of a recombinant nucleic acid encoding the peptide, e.g., using known recombinant expression methods. Thus, in some embodiments a peptide is isolated, purified or substantially pure, i.e., separated from or substantially free of naturally associated components. Purity can be measured by any appropriate method, e.g., column chromatography, polyacrylamide gel electrophoresis, or by HPLC analysis.

It will be understood that a peptide which is chemically synthesized or produced in a cellular system different from the cell from which it naturally originates will be substantially free of its naturally associated components. Accordingly, substantially pure peptides include those derived from eukaryotic organisms but synthesized in E. coli or other prokaryotes.

In some embodiments, a peptide of the invention is provided in the form of a fusion product. For example, a peptide may be linked to another protein, peptide, or tag, in a single polypeptide. In an embodiment, a peptide is linked to a POI (i.e., a target protein). A peptide may be fused N-terminal or C-terminal to a POI in a polypeptide. The invention thus further provides fusion proteins between any protein of interest linked to at least one peptide of the invention. This fusion protein can optionally contain additional peptide tags, such as a polyhistidine peptide tag, an epitope tag, a marker enzyme, etc.

The invention also provides nucleic acids encoding peptides and fusion products described herein. The term "nucleic acid" refers to a polymeric form of nucleotides. By "isolated nucleic acid" is meant a nucleic acid that is no longer immediately contiguous with both of the coding sequences with which it was immediately contiguous (one on the 5' end and one on the 3' end) in the naturally occurring genome of the organism from which it is derived. As such, the term "isolated nucleic acid" includes, for example, a recombinant DNA, which can be incorporated into a vector, including an autonomously replicating plasmid or virus; or into the genomic DNA of a prokaryotic or eukaryotic cell or organism; or that exists as a separate molecule (e.g., a cDNA) independent of other sequences. The nucleotides of the disclosure can be ribonucleotides, deoxyribonucleotides, or modified forms thereof, and nucleic acids can be single stranded or double stranded. Thus, a nucleic acid can be a DNA, an RNA, an oligonucleotide, or an oligonucleoside.

It will be understood that, because of the degeneracy of the genetic code, a large number of functionally identical nucleic acids encode any given peptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded peptide. Accordingly, each variation of a nucleic acid that does not change the sequence of the encoded peptide is intended to be encompassed herein.

In an embodiment, a nucleic acid encoding a peptide of the invention is incorporated into a vector, e.g., an expression vector, or a vector for transfection (which may be stable or transient) in a host cell. In one embodiment, a vector is an expression vector. The term "expression vector" refers to an oligonucleotide which encodes the peptide of the invention and provides the sequences necessary for its expression in a selected host cell. Expression vectors generally include a transcriptional promoter and terminator, or will provide for incorporation adjacent to an endogenous promoter. Expression vectors are typically plasmids, further comprising an origin of replication and one or more selectable markers. However, expression vectors may alternatively be viral recombinants designed to infect the host, or integrating vectors designed to integrate at a preferred site within the host's genome. Examples of viral recombinants are Adeno-associated virus (AAV), Adenovirus, Herpesvirus, Poxvirus, Retrovirus, and other RNA or DNA viral expression vectors known in the art. In an embodiment, a vector is a cloning vector, e.g., a vector for propagating a nucleic acid in a cell.

As used herein, the term "nucleic acid coding for expression of" or "nucleic acid encoding" a peptide or polypeptide refers to a sequence that, upon transcription and translation of mRNA, produces the peptide or polypeptide. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

The construction of expression vectors and the expression of genes in transfected cells involve the use of molecular cloning techniques that are well known in the art. Such techniques include, e.g., in vitro recombinant DNA techniques, synthetic techniques and in vivo recombination/genetic recombination. See, for example, Sambrook et al., Molecular Cloning-A Laboratory Manual, Cold Spring Harbor Laboratory, Cold Spring Harbor, N.Y., (1989) and Current Protocols in Molecular Biology, F. M. Ausubel et al., eds., (Current Protocols, a joint venture between Greene Publishing Associates, Inc. and John Wiley & Sons, Inc., most recent Supplement).

In some embodiments, a nucleic acid encoding a peptide of the invention is genetically fused to a nucleic acid encoding a POI. Thus, in some embodiments there are provided fusion constructs comprising a nucleic acid encoding a peptide of the invention operatively linked to a nucleic acid encoding a POI. The relative positions of the peptide and the POI in the encoded polypeptide are not meant to be particularly limited. For example, the peptide may be fused N-terminal to the POI in the encoded polypeptide, C-terminal to the POI in the encoded polypeptide, or inserted in a flexible loop of the POI in the encoded polypeptide, etc. The term "operatively linked" refers to a juxtaposition wherein the components so described are in a relationship permitting them to function in their intended manner. With reference to nucleic acids that are operatively linked, each distinct nucleic acid molecule is ligated in such a way so as to encode a polypeptide that is functional for its intended purpose. For example, an expression control sequence operatively linked to a coding sequence is ligated such that expression of the coding sequence is achieved under conditions compatible with the expression control sequences.

Transformation of a host cell with a recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the peptide or fusion product of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see, e.g., Eukaryotic Viral Vectors, Cold Spring Harbor Laboratory, Gluzman ed., 1982). Techniques for the isolation and purification of peptides and polypeptides of the invention expressed in prokaryotes or eukaryotes may be by any conventional means such as, for example, preparative chromatographic separations and immunological separations such as those involving the use of monoclonal or polyclonal antibodies or antigen.

Thus, the invention also provides cells comprising the nucleic acids, vectors, peptides, and/or polypeptides of the invention. A cell may be a host cell used for expression and synthesis of a peptide. A cell may also be a cell in which it is desired to visualize a protein of interest, for example a particular cell type (in culture or in situ in an animal) in which it is desired to visualize the localization or trafficking of the POI. A cell may be, for example, a bacterial cell such as an *E. coli* cell, or an animal cell such as a mammalian cell, an invertebrate cell, or a vertebrate cell, e.g., a human cell, a rodent cell, a mouse cell, a rat cell, an insect cell, a yeast cell, a nematode cell, or a fish cell.

Dimaleimide Fluorescent Labelling Agents

Dimaleimide fluorescent labelling agents have been described previously, for example in U.S. Pat. Nos. 7,700, 375; 8,835,641; U.S. Patent Application Publication No. 2015-0316557; Chen, Y. et al., Angew. Chem. Int. Ed. Engl. 53, 13785-13788, 2014; Caron, K. et al., Org. Biomol. Chem. 9, 185-197, 2011; Guy, J. et al., Mol. Biosyst. 6: 976-987, 2010; Guy, J. et al., J. Am. Chem. Soc. 129, 11969-11977, 2007; and Girouard, S. et al., J. Am. Chem. Soc. 127, 559-566, 2005, the entire contents of each of which is hereby incorporated by reference.

The dimaleimide fluorescent labelling agent for use in methods provided herein is not meant to be particularly limited. It should be understood that any dimaleimide fluorescent labelling agent that reacts specifically with the peptides provided herein and is suitable for use in methods of the invention may be used.

It is noted that a dimaleimide fluorogen must undergo two thiol addition reactions before its latent fluorescence is restored. In methods provided herein, a fluorogenic response is selective for a POI linked (e.g., genetically fused) to a peptide of the invention presenting two Cys residues, separated by two turns of the α-helix (~10 Å), because very few native proteins present two free Cys residues on their surface, ~10 Å apart.

In general, a dimaleimide fluorescent labelling agent will include a dimaleimide moiety or reactive unit linked to a fluorogenic core, such as coumarin or a derivative thereof, or another fluorophore (many of which are known in the art). It is generally desirable that fluorescence of the core is quenched until the maleimide groups undergo a specific thiol addition reaction, e.g., with the complementary α-helical peptide of the invention bearing two cysteine residues appropriately positioned to react with the fluorescent labelling agent. For methods provided herein, it is generally desirable that the maleimide groups are positioned around the core in such a manner that they are separated by about 10 Å, in order to be complementary to peptides of the invention.

A dimaleimide fluorescent labelling agent may comprise a symmetric or a non-symmetric dimaleimide moiety. In some embodiments, a dimaleimide fluorescent labelling agent comprises a dimaleimide moiety covalently linked to a coumarin derivative directly or via a linker, such as piperazine (diamide), sulfonamide, alkyne (e.g., acetylene linkage), triazole, urea, thiourea, or ketone. In other embodiments, a dimaleimide fluorescent labelling agent comprises a coumarin derivative linked directly to a dimaleimide moiety by a direct amide linkage with the common aryl on the dimaleimide moiety. In other embodiments, a dimaleimide fluorescent labelling agent comprises a coumarin derivative linked directly to a dimaleimide aryl moiety. In some embodiments, a coumarin derivative is linked directly to a dimaleimide moiety by a single bond, such as diarylamine, diarylether, and diarylthioether.

In some embodiments, a dimaleimide fluorogenic labelling agent comprises a compound of Formula I, or a salt thereof:

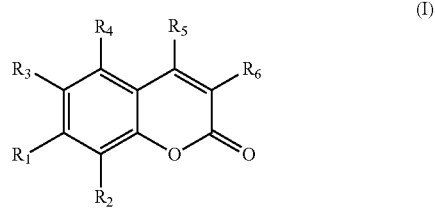

(I)

where:

$R_1$ is $OR_1'$ or $NR_2'R_3'$, wherein $R_1'$, $R_2'$ and $R_3'$ are independently selected from hydrogen, alkyl, alkenyl, alkynyl, cycloalkyl, cycloalkenyl, cycloalkynyl, aryl, alkaryl, arylalkyl, and carboxy alkyl, and $R_1'$, $R_2'$ and $R_3'$ are optionally substituted independently by hydroxyl, amino, carboxyl, carboxylic ester, amide, carbamate, or aminoalkyl; or $R_1'$ and $R_2$ or $R_1'$ and $R_3$ come together to form a 5, 6 or 7-membered ring which is selected from aryl, heterocyclic, heteroaryl, and heteroaromatic; or $R_2'$, $R_2$, $R_3'$, and $R_3$ come together independently to form at least one 5, 6 or 7-membered ring which is selected from aryl, heterocyclic, heteroaryl and heteroaromatic;

$R_2$, $R_3$ and $R_4$ are independently selected from hydrogen, alkyl, alkenyl, alkynyl, cycloalkyl, cycloalkenyl, cycloalkynyl, aryl, alkaryl, arylalkyl, carboxy alkyl, aryl, heterocyclic, heteroaryl, and heteroaromatic, and $R_2$, $R_3$, and $R_4$ are optionally substituted independently by hydroxyl, amino, carboxyl, carboxylic ester, amide, carbamate, or aminoalkyl;

$R_5$ and $R_6$ are independently selected from hydrogen, halogen, alkyl, alkoxy, keto, carboxylate, carboxylic ester, carbamate, amide, amino, alkylamino, polyether, alkylthio, cyano, nitro, sulfonyl, $X_1$, and $X_2$, wherein one of $R_5$ and $R_6$ is $X_1$ or $X_2$, and $R_5$ and $R_6$ are optionally substituted independently by hydroxyl, amino, carboxyl, carboxylic ester, amide, carbamate, or aminoalkyl;

$X_1$ is

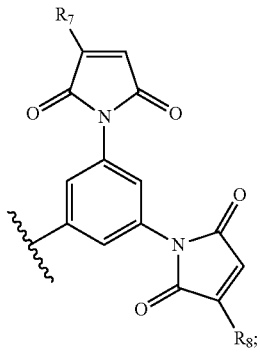

$X_2$ is

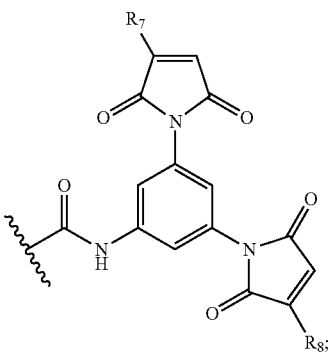

and $R_7$ and $R_8$ are independently $R_9$ or $OR_{10}$, wherein $R_9$ is selected from hydrogen, halogen, and alkyl, alkyl being optionally substituted by hydroxyl, amino, carboxyl, carboxylic ester, amide, carbamate, or aminoalkyl, and $R_{10}$ is alkyl, alkyl being optionally substituted by hydroxyl, amino, carboxyl, carboxylic ester, amide, carbamate, or aminoalkyl.

In some embodiments, a dimaleimide fluorogenic labelling agent comprises a compound of Formula (II), or a salt thereof:

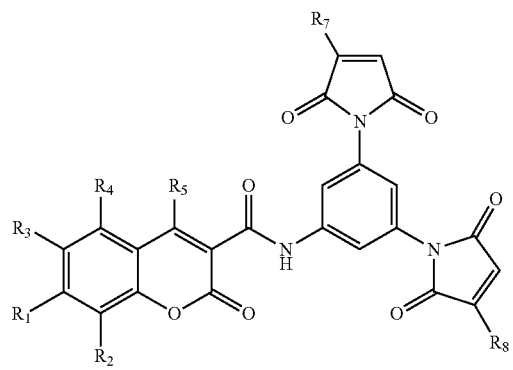

wherein $R_1$ to $R_8$ are as defined above.

In some embodiments, a dimaleimide fluorogenic labelling agent comprises a compound of Formula (III), or a salt thereof:

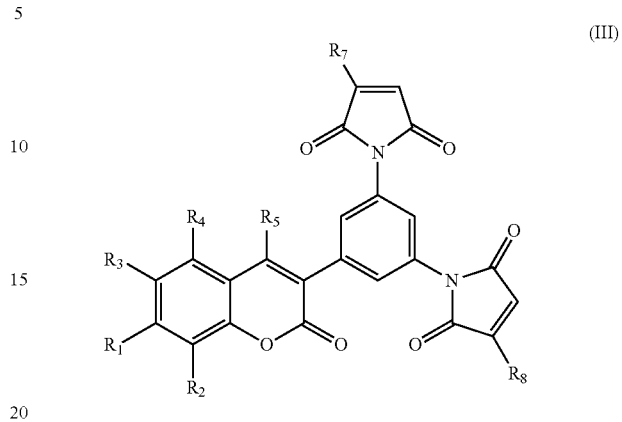

wherein $R_1$ to $R_8$ are as defined above.

In some embodiments, a dimaleimide fluorogenic labelling agent comprises a compound of Formula (IV), or a salt thereof:

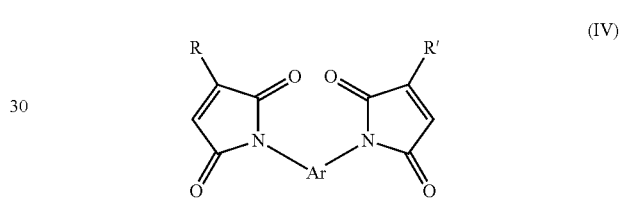

wherein each R or R' is independently $R_a$ or $OR_a$, and $R_a$ is H, $C_1$-$C_4$ alkyl, $CH_2CO_2H$, $CH_2CH_2OH$ or CN and Ar is a rigid aromatic skeleton selected from the group consisting of fluorescein, rhodamine, eosin, thionine, safranin, fluorescent derivatives having naphthyl groups and coumarin.

In some embodiments, a dimaleimide fluorogenic labelling agent comprises a compound of Formula (V), or a salt thereof:

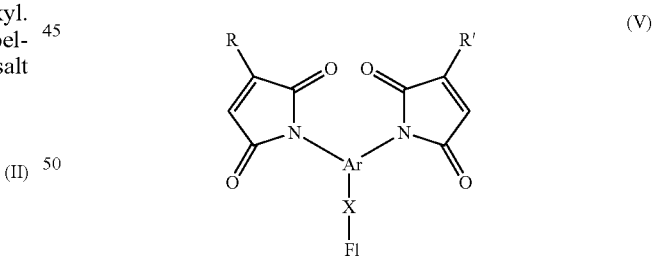

wherein each R or R' is independently $R_a$ or $OR_a$, and $R_a$ is H, $C_1$-$C_4$ alkyl, $CH_2CO_2H$, $CH_2CH_2OH$ or CN and Ar is a rigid aromatic skeleton comprising one aromatic ring or two or more fused aromatic rings selected from the group consisting of phenyl, naphthyl, anthracene, fluorene, pyridine, pyrimidine, purine, and indole, X is a spacer sequence selected from the group consisting of $C_1$-$C_4$ alkyl, $OCH_2CH_2O$, $NHCO(C_1$-$C_4CH_2$alkyl)$NHCO,CONH(C_1$-$C_4CH_2$alkyl)CONH, $NHCO(C1$-$C_4CH_2$alkyl)CONH, $CONH(C_1$-$C_4CH_2$alkyl)CONH, and Fl is a fluorophore selected from the group consisting of selected from the group consisting of fluorescein, rhodamine, eosin, thionine, safranin, and coumarin.

In some embodiments, a dimaleimide fluorogenic labelling agent comprises a compound of Formula (VI), or a salt thereof:

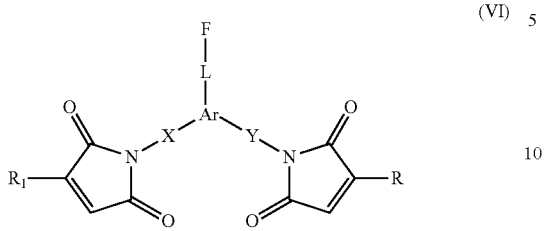

wherein X and Y are independently or together absent or are independently selected from

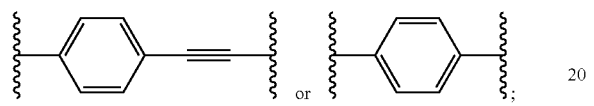

R and R₁ are independently selected from H and alkyl; Ar is phenyl or heteroaryl; L is absent or a spacer selected from the group consisting of —NH—; —(CH₂)ₙNH—; —NHSO₂—; —(CH₂)ₙNHCO—; -(cycloalkyl)NHCO—; —(CH₂)ₙNHSO₂—; -(cycloalkyl)NHSO₂—; —CONH(CH₂)ₙNHCO—; —CONH(cycloalkyl)NHCO—; —NHCO(CH₂)ₙNHCO—; —NHCO(cycloalkyl)NHCO—; —(CH₂)ₙSO₂NH—; -(cycloalkyl)SO₂NH—; —(CH₂)ₙNHCSNH—; -(cycloalkyl)NHCSNH—; —CR=CR₁—; —C≡C—; —(CH₂)ₙN=CH—; -(cycloalkyl)N=CH—; —N=CH(CH₂)—; —N=CH(cycloalkyl)-;

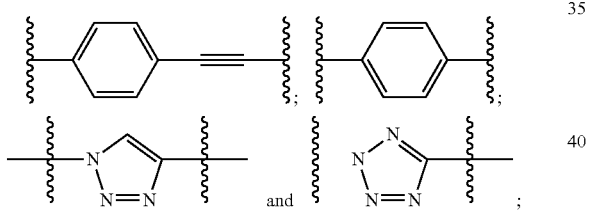

n is an integer ranging from 1 to 5; F is a fluorophore selected from the group consisting of fluorescein, rhodamine, eosin, thionine, safranin, coumarin, methoxycoumarin, dansyl, BODIPY and BODIPY derivatives; and wherein X, Y and L may be positioned in a 1,3,5; 1,2,3; 1,3,4 or in a 3,4,5 configuration respectively.

In some embodiments, a dimaleimide fluorogenic labelling agent is

1

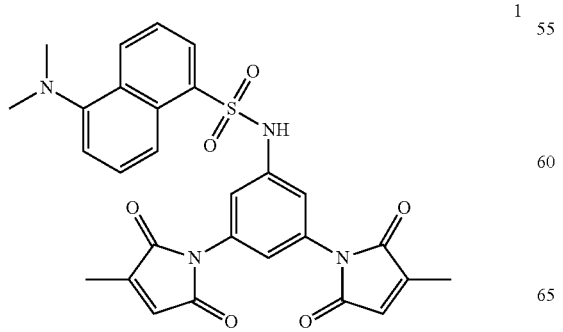

2

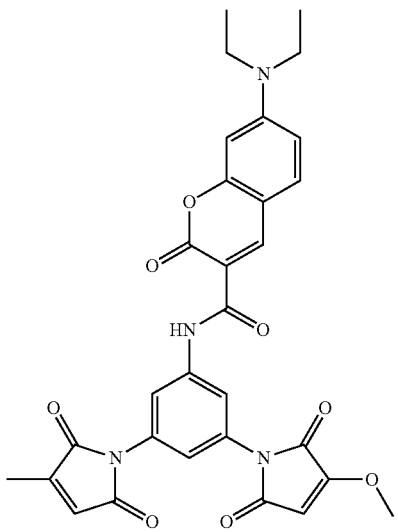

3

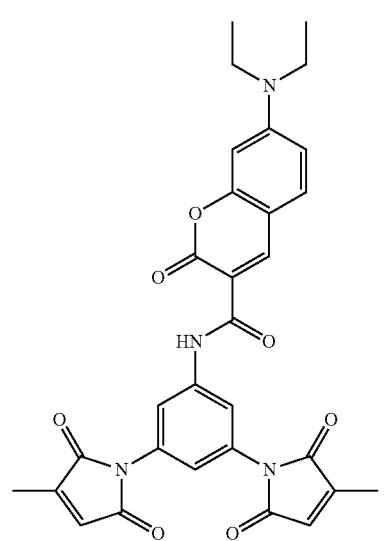

4

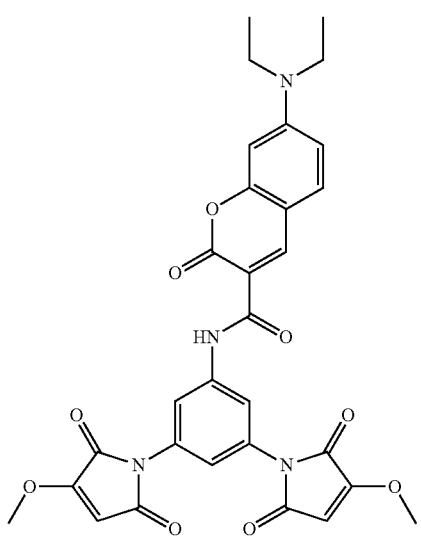

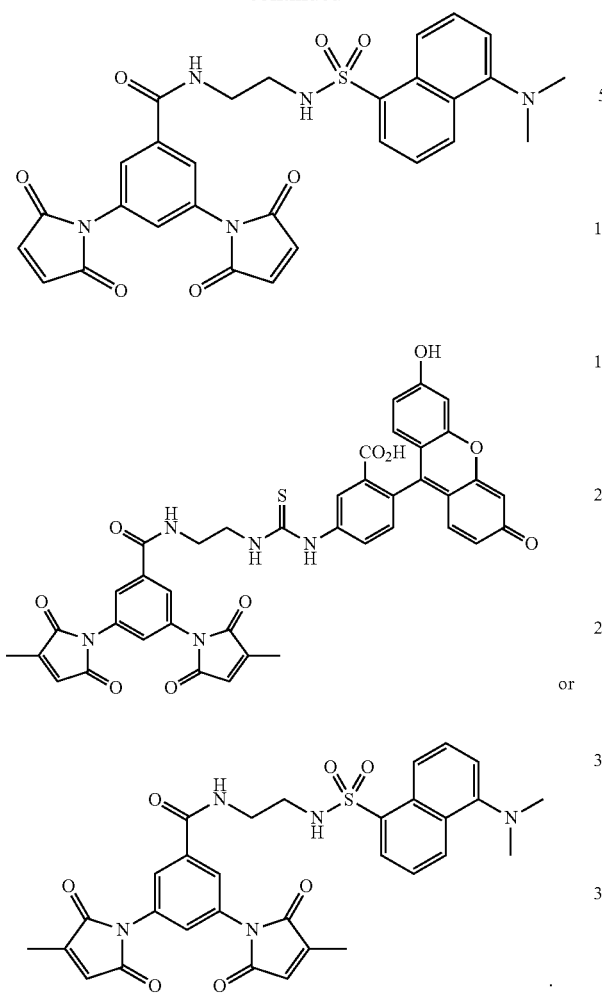
In some embodiments, a dimaleimide fluorogenic labelling agent is a compound selected from:
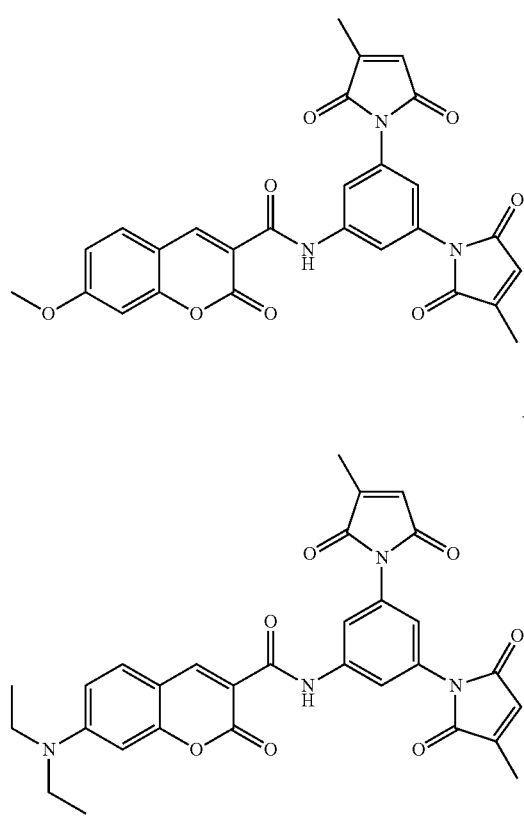
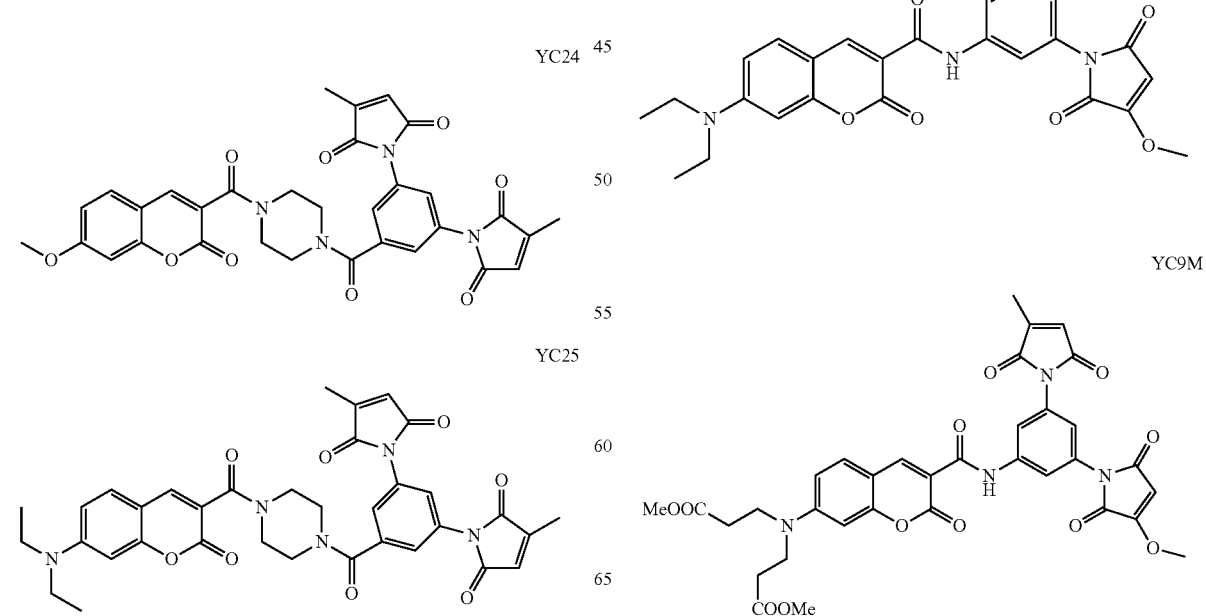

YC9A

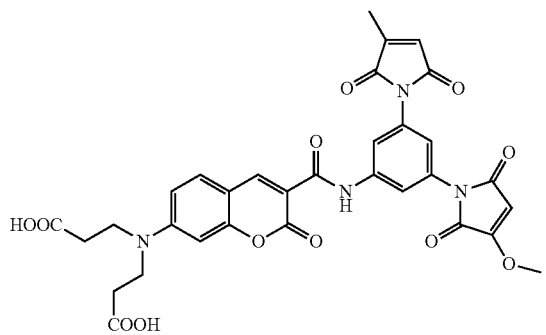

YC21A

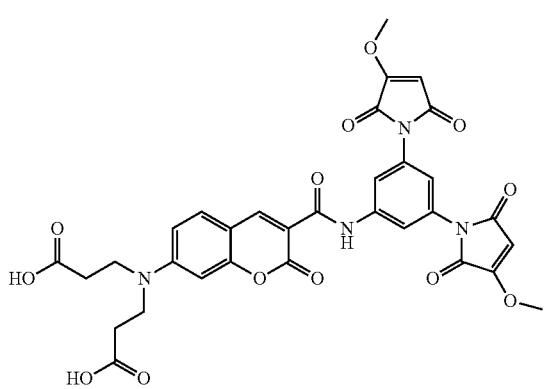

YC15-YC19

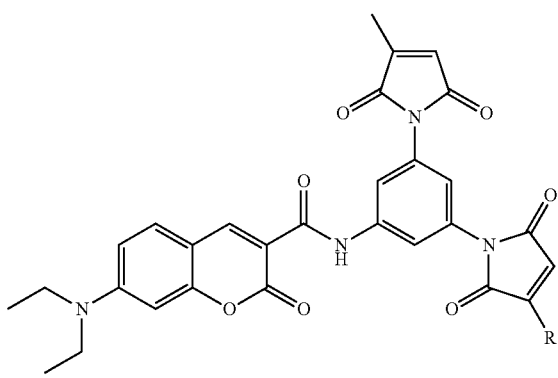

R = Et  YC15
$^i$Pr  YC16
OEt  YC17
Br  YC18
O$^i$Pr  YC19

YC20

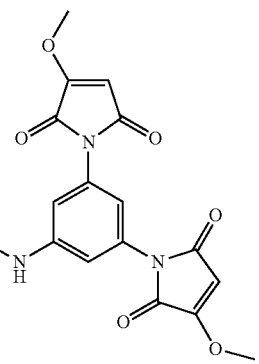

YC21M and salts thereof.

Labelling Methods

There are provided herein methods of labelling and/or detecting specific protein targets, and methods of live imaging, using peptides of the invention in FlARe labelling techniques. In methods provided herein, peptides of the invention are used to tag proteins of interest (POIs; also referred to herein as "target" proteins). Generally, the fluorescence of a dimaleimide fluorescent labelling agent is quenched before reaction with a peptide of the invention; fluorescence is only detected after the dimaleimide fluorescent labelling agent has reacted with the peptide linked to a target protein, detection of fluorescence thus indicating that reaction has occurred, and thereby indicating the presence of the target protein. In some embodiments, some fluorescence may be detected before the fluorescent labelling agent has reacted with the target protein (e.g., before labelling), and fluorescence increases after the fluorescent labelling agent has reacted with the target protein, such that an increase in fluorescence indicates that reaction has occurred, thereby indicating presence of the target protein.

Methods provided herein may be used to label and/or detect specific protein targets in vitro, in vivo, or ex vivo. In some embodiments, methods are used in living cells for "live imaging," allowing visualization of a target protein's expression, localization, trafficking, and/or interactions inside a cell, or inside a living organism. The methods may therefore provide valuable information about the function of target proteins that cannot be uncovered in vitro. Thus in some embodiments, reaction of a dimaleimide fluorescent labelling agent and a target protein (fused to a peptide of the invention) occurs in a living cell. "Living cell" is not meant to be particularly limited. For example, a living cell may be a cultured cell, of which many types are known (e.g., a primary culture, a cell line, a transformed cell line, an immortalized cell, etc.), or a living cell may be present in an organism, such as a transgenic animal, etc.

In some embodiments, a cell, e.g., a living cell, is an animal cell. Non-limiting examples of animal cells include mammalian cells, invertebrate cells, vertebrate cells, human cells, rodent cells, mouse cells, rat cells, yeast cells, insect cells, nematode cells, and fish cells.

In some embodiments of methods provided herein, a target protein is an intracellular protein. In some embodiments, a target protein is an extracellular or cell-surface protein. It will be understood that a dimaleimide fluorescent labelling agent may react with, or label, a target protein intracellularly or extracellularly, depending on where the target protein is localized. In some embodiments, characteristics of the fluorescent labelling agent are sufficient to allow intracellular labelling. For example, the fluorescent labelling agent may have one or more of the following characteristics: selectivity/high specificity for the target protein; lack of background reactivity (e.g., lack of reaction with cellular proteins or glutathione); and efficient quenching of fluorescence before reaction with the target protein, coupled with bright fluorescence after reaction with the target protein. In the context of background reactivity, "lack of reaction with cellular proteins" is meant to refer to lack of reaction with native cellular proteins that are not linked, e.g., genetically fused, to a peptide of the invention.

In some embodiments of methods provided herein, the target protein has been genetically engineered to include a peptide of the invention. For methods conducted in vitro, for example, a fusion product comprising a target protein and a peptide of the invention may be synthesized in vitro or may be purified from a cell genetically engineered to express the fusion product. For methods conducted in vivo or ex vivo, in some embodiments a cell or organism may be genetically engineered to express the target protein comprising the peptide (e.g., as a fusion product). Many such methods are known in the art.

In some embodiments, methods provided herein are particularly advantageous for live imaging, due to the small size of the peptide of the invention used to tag the target protein. In some embodiments, the peptide sequence or tag on the target protein does not significantly alter the function or localization of the target protein.

Many methods for detecting fluorescence are known and may be used in methods provided herein. Non-limiting examples of techniques used to detect fluorescence include fluorescence microscopy (e.g., with a fluorescence microscope, a confocal microscope, a total internal reflection fluorescence microscope (TIRFM), etc.); fluorescence spectroscopy (e.g., with a filter fluorometer, a spectrofluorometer, etc.); fluorescence resonance energy transfer (FRET); plate readers (e.g., microplate readers); HPLC fluorescence detectors; and so on. One skilled in the art will select the appropriate method of detecting fluorescence in accordance with the particular application or target protein being studied.

In some embodiments, an agent or method provided herein may be used in conjunction with a second labelling agent to detect a second target protein, for example in a double labelling experiment to allow simultaneous detection or visualization of two different target proteins, or to assay biomolecular interactions between two target proteins. In such experiments, typically the second labelling agent fluoresces at a different wavelength from the first fluorescent labelling agent, so that the two fluorescent signals can be distinguished. For example, there are provided methods for assaying biomolecular interactions between a first target protein and a second target protein, wherein the first target protein and the second target protein are linked to a first peptide of the invention and a second peptide of the invention, respectively, for binding to a first fluorescent labelling agent and a second fluorescent labelling agent, respectively; the first target protein and the second target protein are contacted with the first fluorescent labelling agent and the second fluorescent labelling agent, respectively; and fluorescence of the first fluorescent labelling agent and the second fluorescent labelling agent are detected. The first and second fluorescent labelling agents may comprise two different fluorogens, permitting detection of their interaction through a FRET-based fluorescent assay, for example. It will be appreciated that in addition to protein-protein interactions, other molecular interactions, such as protein-small molecule, protein-nucleic acid and protein-carbohydrate interactions, may be detected using similar methods.

The invention further provides kits for labelling and/or detecting a target protein fused to a peptide of the invention. Kits may further comprise a dimaleimide fluorescent labelling agent, and/or instructions for use. A kit may also include reagents, solvents, buffers, etc., required for carrying out the methods described herein. In some embodiments, a kit includes a peptide of the invention. In some embodiments, a kit includes a vector encoding a peptide of the invention, suitable for use in cloning or expressing the peptide. The vector may also encode a fusion product, e.g., a protein of interest fused to a peptide of the invention. Kits for live imaging of target proteins and for assaying biomolecular interactions are also provided.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Example 1. Preliminary dC10 Mutants

Previously, an attempt was made to improve the stability of the reactive thiolates of C13 and C6 in dC10 by introducing a histidine residue in positions adjacent to C6 (i.e., at position A7), or one turn of the helix away from C13 and/or C6 (i.e., at positions R9 or S2) (Guy, J. et al., Mol. Biosyst. 6: 976-987 (2010)). Histidine mutations were rationally chosen since these residues are known to be excellent proton donors and acceptors at physiological pH due to the pKa of their side chain imidazole group. Some double mutants were also created, where A17 and S2 (one turn away from reactive C6 and C13) were both replaced by histidine. Second order rate constants were then measured for the reaction of these mutant sequences with the FITC-dM10 fluorogen. None of the mutant sequences exhibited better reactivity than the parent dC10 peptide, possibly due to the potential destabilization of the mutant dC10 helices by the histidine residues (Pace, C. N. and Scholtz. J. M., Biophys. J., 75: 422-427, 1998).

We therefore decided to undertake a more combinatorial approach towards dC10 sequence optimization. We started by using a combinatorial approach to explore a larger ensemble of mutants, and then used these results as a basis for a rational second and third step of new tag design. Using this rational design we have engineered new peptide tags with faster reactivity than the parent dC10 peptide tag.

Figure 4:
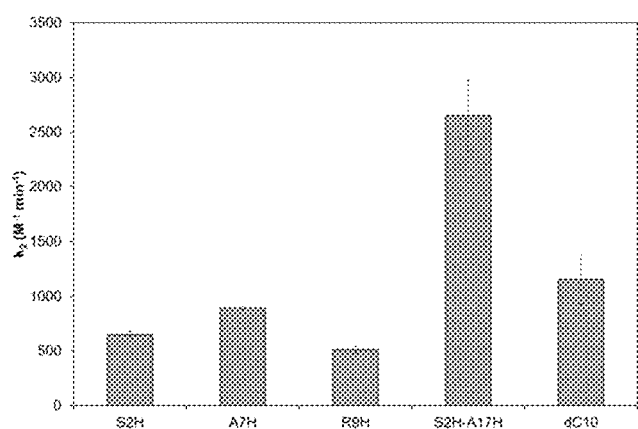
FIG. 4 shows second order kinetic constants for single and double mutants previously characterized (Guy, J. et al., Mol. Biosyst. 6: 976-987, 2010) and the dC10 peptide, as indicated, where kinetics of addition of fluorogen 1 was performed at 20° C. in a Cary Eclipse fluorimeter, in duplicate; error bars are shown.

To start, we used fluorogen 1. These new results demonstrated that the double mutant S2H-A17H was more reactive than the parent dC10 (FIG. 4). However, the single mutants S2H, A7H and R9H did not appear to be more reactive than dC10, leading us to hypothesize that only the histidine mutation at position 17 is responsible for the greater reactivity of the double mutant S2H-A17H.

After identifying position 17 as a potential 'hotspot' for reactivity, we expanded the variety of residues at that position by creating an eight-member library, substituting A17 with a charged (D, E, H, K, R) or polar (N, Q, S) residue. For that purpose we used DNA oligonucleotides containing the degenerate codon VRN that encodes all the above mentioned positive or polar residues, plus a glycine residue (see Materials and Methods section). However, the glycine mutant was of little interest to us, since glycine is known to disrupt helices and is not able to interact with other residues by charge-charge stabilization.

Example 2. Protein Expression and Purification, and Kinetic Characterization of Mutants from Library I Peptide sequences were expressed as fusion products with the maltose binding protein (MBP) as a test protein, since MBP can be easily expressed in significant quantities and in soluble form. Plasmids for MBP-dC10 point mutant expression were prepared as described in the Materials and Methods section. MBP-dC10 variants were expressed and purified in a very high yield of 5-15 mg of pure protein from 250-350 mL of expression media.

Figure 5:
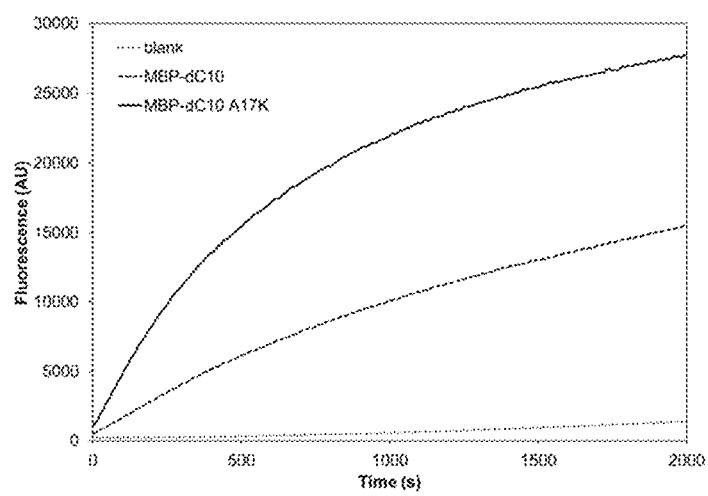
FIG. 5 shows fluorogenic addition reaction kinetics of MBP-dC10 and fluorogen 1, where a comparison of background hydrolysis of fluorogen 1 (dotted line) versus reactivity with MBP-dC10 (dashed line) and a point mutant MBP-dC10 A17K (full line) is shown.

The reactivity of each single mutant of MBP-dC10 was evaluated through their reaction with dansyl-dM10 fluorogen 1 (Caron, K. et al., Org. Biomol. Chem., 9: 185-197, 2011), commonly used for test purposes. Equimolar concentrations of 50 µM of fluorogen 1 and MBP-dC10 variant were used in pH 7.5 buffer HEPES 50 mM, supplemented with 1 mM of TCEP reducing agent to reduce disulfide bonds that could form during protein purification or storage. Incubation of fluorogen 1 alone in buffer showed that reaction between TCEP and dansyl-dM10 can occur (FIG. 5), but it does so only after a longer period of time than fluorogen addition on MBP-dC10. Hence, for the measurement of rate constants, the rate of background hydrolysis was subtracted, and all reactions were performed in buffer supplemented with 1 mM TCEP, to ensure that all thiols were reduced and reactive.

Progress curves of the fluorogenic addition reaction were acquired with a plate reader that allowed us to study a large number of samples at the same time. Since the dansyl fluorophore is sensitive to its environment, the reaction of each MBP-dC10 variant led to an end point of slightly different fluorescence intensity. We used a simple second order kinetic model A+B→C where reactants A and B were used in equimolar concentrations. The product C is the only fluorescent species in the milieu and its appearance can be directly followed by increase of fluorescence. Use of this model implies that the second thiol addition is extremely fast due to its intramolecular character, and that the second order kinetic constant $k_2$ depends exclusively on the first thiol addition. This reasonable approximation allowed us to evaluate very simply the overall dC10 reactivity modulated by the presence of stabilizing residues in the proximity of cysteines C6 and C13.

The second order rate constants determined for single mutants of MBP-dC10 (FIG. 6) showed that negatively charged (D and E) or polar (N, Q and S) residues fail to significantly improve the reactivity of dC10 thiols. In the case of D and E this is probably due to the low pKa of their side chain carboxylic acids, resulting in the formation of carboxylates which disfavour the formation of an adjacent thiolate. Conversely, the positively charged residues (H, K and R) showed a 1.5- to 2.5-fold enhancement in the second order rate constant. The reactive species in a thiol—maleimide addition reaction is most likely a thiolate, normally present in a very small proportion at neutral pH due to the higher pKa of the cysteine side chain (determined to be 8.55 in an alanine pentapeptide (Thurlkill, R. L. et al., Protein Sci. 15: 1214-1218, 2006), or in a range of 7.4-9.1 in various peptides (Bulaj, G. et al., Biochemistry 37: 8965-8972, 1998), or as high as 9.5 for cysteine-like compounds (Tanford, C., Advanced Protein Chemistry 17: 69-165, 1962; Nozaki, Y. and Tanford, C., Methods in Enzymology 11: 715-734, 1967). This suggests that adjacent positively charged residues may stabilize the thiolate form through electrostatic interaction, decreasing the pKa of the dC10 cysteine side chain and increasing the proportion of reactive thiolate.

A second contribution to be considered in the dC10/dimaleimide reaction is the helical conformation of the dC10 peptide. It was shown previously (Girouard, S. et al., J. Am. Chem. Soc. 127: 559-566, 2005) that thiols presented in a helical conformation react faster with dimaleimides than simple free thiols. Indeed, the dimensions and geometry of our dimaleimide fluorogens are designed to complement the thiols presented in our dicysteine helical motif. Thus, we can presume that the propensity of the peptide to adopt a helical conformation is another condition required for optimal reactivity of both thiols of the dC10 peptide. In general, it is known that the ability of each residue to favor a helical conformation varies substantially. While alanine residues are the most prone to form a stable helix, residues such as glycine or proline strongly disfavour a helical conformation. Therefore, replacing an alanine with a mutant residue will inevitably destabilize the dC10 helix to a greater or lesser extent. A scale of propensity for all investigated residues is presented in FIG. 7 and shows that the least reactive mutants are not only unfavorable for thiolate stabilization (D, E, N, Q, S), but also the least prone to stabilize a helix. Furthermore, it is possible that histidine, thought to increase the reactivity of the peptide sequence by favoring formation of thiolate, may also disfavour the reactivity by perturbing the formation of a reactive helix conformation. For example, our results (FIG. 7) show that while the single histidine mutant A17H reacts faster than the parent dC10 peptide tag, it does not react as fast as the A17K mutant, possibly due to destabilization of the helical conformation required for optimal reactivity with dimaleimide fluorogen.

Figure 6:
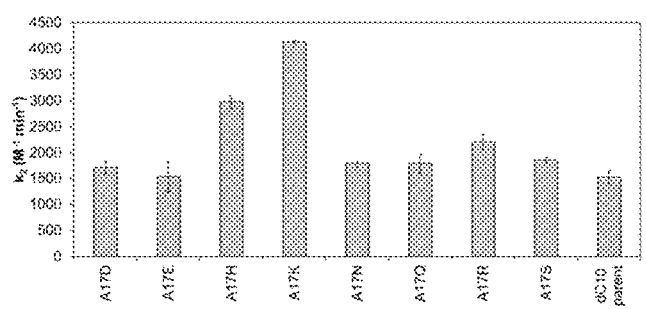
FIG. 6 shows second order rate constants for MBP-dC10 library I; all reactions were performed at equimolar concentration of 50 μM of fluorogen 1 and MBP-dC10 or variant, as indicated, in duplicate, on a Synergy™ H4 plate reader at 28° C., and fluorescence increase was observed at 515 nm upon excitation at 330 nm.
Figure 7:
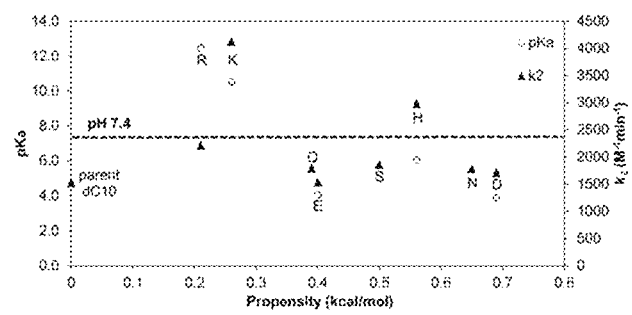
FIG. 7 shows propensity and pKa of individual residues used in MBP-dC10 single mutant library I, where propensity values represent the destabilization energy of a helix of a given residue relative to alanine. For the single mutant library A17X, the pKa of each residue X is shown (circles, left vertical axis) along with the measured second order rate constant (triangles, right vertical axis). The dashed line represents physiological pH of 7.4 to emphasize the expected protonation state of each residue.

The results of our initial screen are shown in FIGS. 6 and 7. Our results show that the best dC10 single mutant was A17K. Without wishing to be bound by theory, this is most likely due to its low helix-destabilizing character and, perhaps more importantly, to the positive charge on its side chain that may electrostatically decrease the pKa of the adjacent cysteine residue.

To overcome the unequal helical propensity of some residues, we investigated possible ways to improve helix content in peptides by using additives. 2,2,2-Trifluoroethanol is a solvent commonly used for this purpose. However, we found that some components of our system were insoluble at high concentrations of trifluoroethanol for which the secondary structure stabilization is strongest, leading to precipitation (data not shown). When used at lower concentrations, trifluoroethanol caused a higher reactivity of all dC10 single mutants from library I, but the order of reactivity with respect to the parent dC10 peptide stayed roughly the same (data not shown).

Example 3. Double and Triple Mutants of dC10—Libraries II and III

Figure 9:
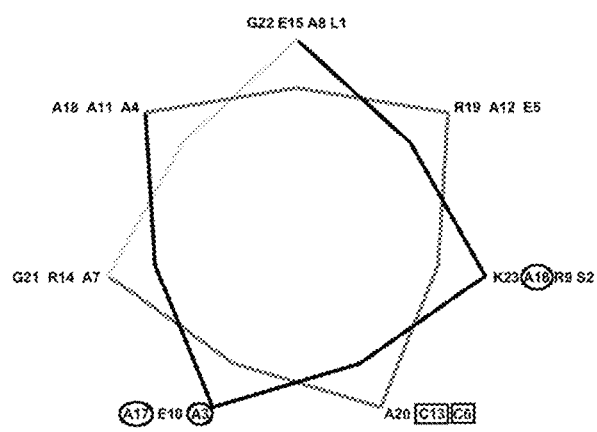
FIG. 9 shows a section view of the dC10 helix, where the first loop involves residues L1, S2, A3 and A4 (black line), the second loop contains residues E5, C6, A7 and A8 (dark grey line), etc. Cysteines C6 and C13 are indicated (black squares) as well as mutation sites A3, A16 and A17 (black circles).

Based on the kinetic results obtained for our single mutant library dC10 A17X, mutant residues H, R and K, having side chains likely to be positively charged at neutral pH, were retained for further mutagenesis studies. FIG. 9 shows the relative proximity of residues in a helical conformation of dC10, from which two other potential candidates for mutagenesis in close proximity to cysteine 13 are apparent. Specifically, alanine 16 and arginine 9 are both one turn away from cysteine 13, and we hypothesized that these residues could potentially have an effect on its ionization state and helix stability. Arginine 9 may already be engaged in a salt bridge with glutamate 5, thereby stabilizing the helical conformation of dC10. When this arginine residue was mutated to a lysine in the mini-library R9K-A17X (where X is H, K or R), none of the double mutants dC10 R9K-A17X showed any further improvement in reactivity in comparison with their single A17X mutant parent sequences (results not shown). These results suggested that the mutation of residues engaged in salt bridge interactions in dC10 is unlikely to lead to more active dC10 variants.

On the other hand, residue alanine 16 is an excellent candidate for mutagenesis because its only stabilizing contribution is its favorable helix propensity. Therefore, we replaced Ala16 with either histidine, lysine or arginine in the mini-library A16X-A17K. Screening of this library (see FIG. 10) confirmed our previous findings with the single mutant library: a reactivity enhancement of up to eight-fold was observed for double mutants relative to the single mutant parent A17K. Double mutant A16H-A17K was not as reactive as double mutants A16K-A17K and A16R-A17K, which is once again consistent with the low helical propensity of histidine (FIG. 7).

Figure 10:
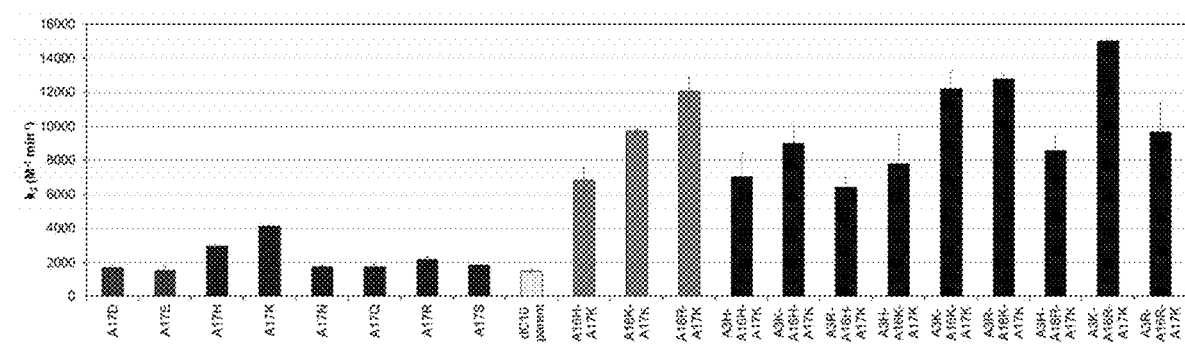
FIG. 10 shows second order kinetic constants determined for MBP-dC10 mutants. Library I with point mutants at position A17 is represented in dark grey, library II with double mutants A16-A17 is represented in light grey, and library III with triple mutants A3-A16-A17 is represented in black. The rate constant for parent MBP-dC10 is represented in white. All measurements were performed at least in duplicate.

Up to this point in the study, the reactivity of the helical sequence was enhanced by mutations at positions 16 and 17, adjacent to cysteine 13. According to FIG. 9, the only residue in close proximity of cysteine 6 that would be likely to affect reactivity is alanine 3. A library of triple mutants was therefore created by preparing all possible combinations of histidine, lysine and arginine at positions 3 and 16, while retaining a lysine residue at position 17. In total, nine triple mutants were isolated and fully characterized kinetically; as shown in FIG. 10, four triple mutants (A3K-A16K-A17K, A3K-A16R-A17K, A3R-A16K-A17K and A3R-A16R-A17K) exhibited a nearly 10-fold increase in reactivity towards a dimaleimide fluorogen, while mutant A3K-A16R-A17K reacted 10 times faster than the parent dC10 sequence. This rate enhancement represents a significant breakthrough for the FlARe labelling technology.

Example 4. Investigation of the Role of Residue 3 of dC10

It is generally assumed that when two covalent bonds are formed between two reactive molecules, the intermolecular reaction to form the first covalent bond is slower than the rapid intramolecular reaction to form the second covalent bond. Thus, while we can explain the enhanced reactivity of cysteine 13 due to the presence of two thiolate-stabilizing residues (at positions 16 and 17), it is not clear how improving the reactivity of cysteine 6 would further enhance the reactivity of the peptide (if the reaction of cysteine 6 were intramolecular). However, this is based on the assumption that in all cases, cysteine 13 is indeed the first to react with a maleimide moiety of a given dimaleimide fluorogen. However, enhancing the nucleophilicity of both cysteine residues would be expected to increase the effective concentration of both reactive cysteine residues in the peptide sequence, thereby increasing the overall rate of reaction regardless of which cysteine residue reacts first. We hypothesized therefore that a A3-A16-A17 triple mutant may react faster than its A16-A17 double mutant, because it contains a higher effective concentration of highly reactive cysteines. As shown in FIG. 10, we found indeed that the triple mutant A3K-A16R-A17K is slightly more reactive than its parent double mutant A16R-A17K, in support of this hypothesis.

Example 5. Quantification of Cysteine pKa Decrease Induced by Mutations

Figure 8:
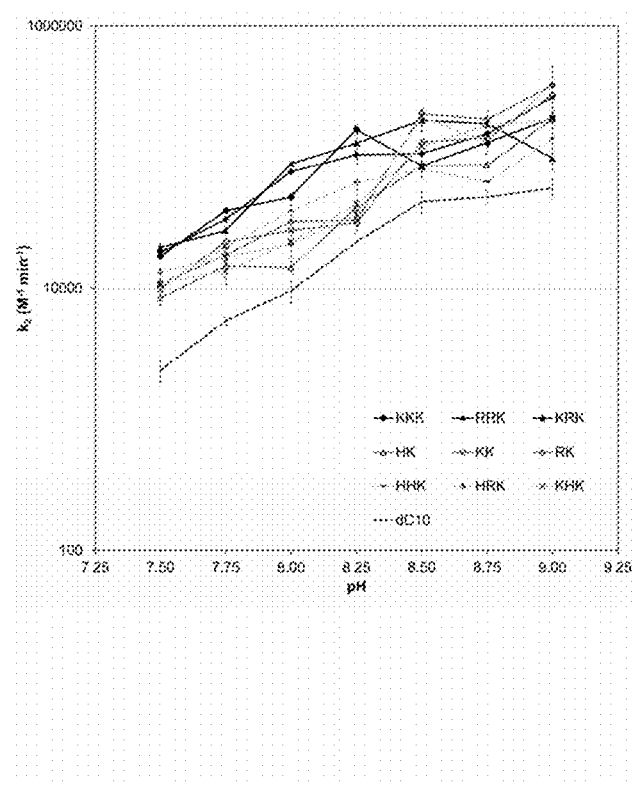
FIG. 8 shows the pH-rate profile for several MBP-dC10 mutants, as indicated. A pH range between 7.50 and 9.00 was explored to determine the dependence of the second order rate constant on pH. Only several mutants from libraries II and III were chosen for this pH study: Triple mutants containing lysine and arginine (black line), triple mutants containing histidine and lysine or arginine (light grey line), double mutants (dark grey line) and parent dC10 (dashed line).

Considering the relative reactivity of the members of all three mutant libraries, additional studies were undertaken to attempt to quantify the effect of positively charged residues on the acidity of the cysteine residue thiol groups. The fluorogenic addition reactions of several selected mutant peptide sequences with a dansyl-dimaleimide fluorogen were studied kinetically over pH 7.50-9.00; higher pH values were practically inaccessible due to protein instability. As shown in FIG. 8, a linear relationship was observed between the logarithm of the measured second order rate constant and the pH of the milieu, confirming that in all cases, the basic form of the peptide was more reactive. From this plot, one can roughly group the mutant sequences into three groups: the triple mutants that do not contain histidine (FIG. 8, black lines), the triple mutants containing histidine (FIG. 8, light grey) and the double mutants (FIG. 8, dark grey). From this plot, it appears from the horizontal displacement of the best fit lines (see below) that the pKa of the fastest mutant (A3K-A16R-A17K) is 0.70 units lower than that of the parent dC10 sequence. This is likely due to increased thiol acidity through local electrostatic effects.

Figure 3:
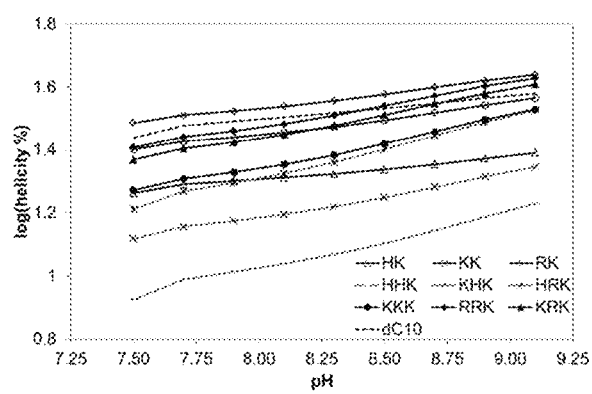
FIG. 3 shows the predicted helicity of dC10 peptides, where helicity was predicted using AGADIR software and complete dC10 or variant peptide sequences (as indicated), with the following parameters: 301 K, ionic strength 0.1 M.

Another pH effect that is important to discuss is the pH dependence of the helical propensity of each residue. We used the online AGADIR algorithm to predict the helical content of the entire dC10 (or variant) sequences at different pH values (Munoz, V. and Serrano, L/Nat. Struct. Biol., 1: 399-409, 1994). As shown in FIG. 3, the logarithm of the percent global helical content of each dC10 sequence increased with pH, in an almost linear fashion over the pH range 7.50-9.00). This predicted increase in helicity may account for a small fraction of the observed increase in reactivity, although the near-unity slopes of the pH-rate profiles shown in FIG. 8 suggest that most of the increased reactivity is due to a single ionization event.

Example 6. Labelling with Coumarin-dM10 In Vitro

Figure 12:
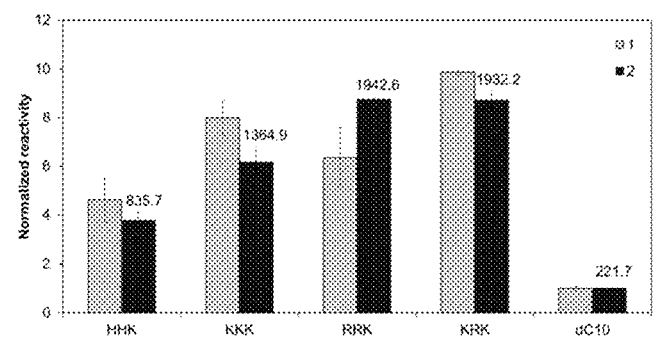
FIG. 12 shows a comparison of the reactivity of fluorogens 1 and 2. Second order rate constant ratios are shown for selected triple mutants (as indicated) of MBP-dC10 and fluorogen 1 (grey), and fluorogen 2 (black). Ratios were obtained by normalizing all rate constants to the rate constant of parent MBP-dC10. Absolute values of second order rate constants in $M^{-1}min^{-1}$ are shown for fluorogen 2. Results were obtained at least in duplicates; average values and error bars are shown. (Values of rate constants obtained with fluorogen 1 are shown in FIG. 10).

To demonstrate the importance of the rate enhancement of dC10 for diverse applications, we next evaluated the in vitro kinetic behavior of several dC10 triple mutants with relevant dimaleimide fluorogens. The second order kinetic constants of these reactions are shown in FIG. 1. Although coumarin fluorogen 2 was much less reactive than dansyl fluorogen 1 (FIG. 12), similar relative reactivities were observed among the dC10 triple mutants. Namely, the second order rate constant of the most reactive dC10 mutant A3K-A16R-A17K was 9 times higher than that of the parent dC10 sequence. This increased reactivity may be especially important for intracellular applications, in order to compensate for attenuated reactivity of the fluorogenic labelling agent (Guy, R. et al., Mol. Biosyst. 6: 976-987, 2010; Chen, Y. et al., Angew. Chem. Int. Ed. Engl. 53: 13785-13788, 2014).

We also tested the in vitro kinetic behavior of the dC15 peptide by fusing it onto Maltose Binding Protein (MBP) using the reverse primer 5'-GGAATTCCTCATTTGCCAC-CCGCGCGACATGCCGCTTCGCGTGCTGCTGCTTC ACGTGCACACGCTTCCGCCGCACTCAGCCTTC-CCTCGATCCC-3' (as described herein). Kinetics of the labelling reaction at 20° C. was studied. The second order kinetic constants of these reactions are given in Table 2 for two fluorogens, as indicated. Rate constants for the reaction with MBP-dC10 are given for comparison.

Example 7. Labelling with Cyan Fluorogens In Vitro and In Cellulo

Figure 13:
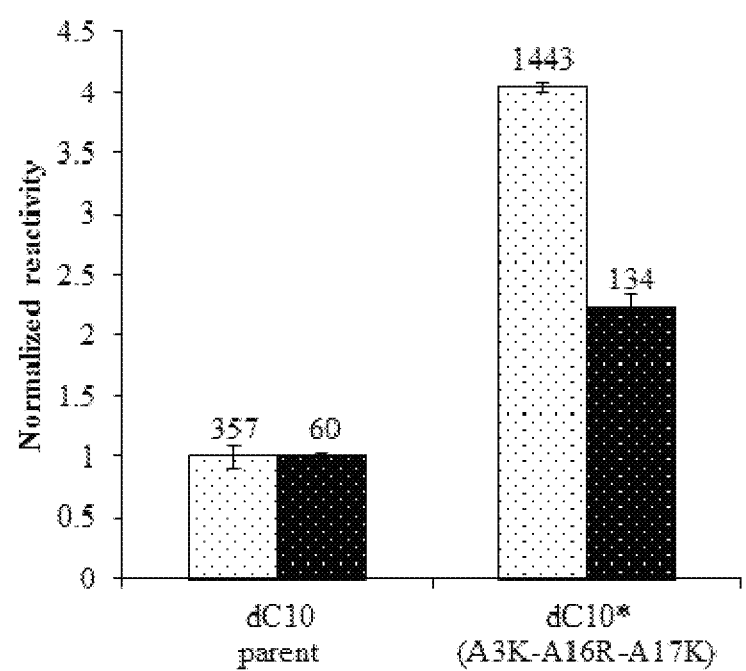
FIG. 13 shows a comparison of in vitro reactivity of fluorogens 3 and 4 with dC10 and dC10* (dC10-A3KA16RA17K). Second order rate constant ratios are shown for fluorogen 3 (grey), and fluorogen 4 (black). Ratios were obtained by normalizing all rate constants to the rate constant of parent MBP-dC10. Absolute values of second order rate constants in $M^{-1}min^{-1}$ are shown for each fluorogen and dC10 or dC10*, and were obtained using equimolar concentration of 50 μM of fluorogen and test protein, at 28° C. Results were obtained at least in duplicate.

To extend the results shown above with fluorogens 1 and 2, we tested whether the labelling of dC10* (dC10-A3KA16RA17K) with other coumarin fluorogens would also show a kinetic advantage compared to dC10. When fluorogen 4 (FIG. 11) was tested in vitro, it showed a 2-fold rate enhancement with dC10* (FIG. 13). Furthermore, methyl-disubstituted fluorogen 3 showed a 4-fold rate enhancement with dC10* (FIG. 13).

Figure 14:
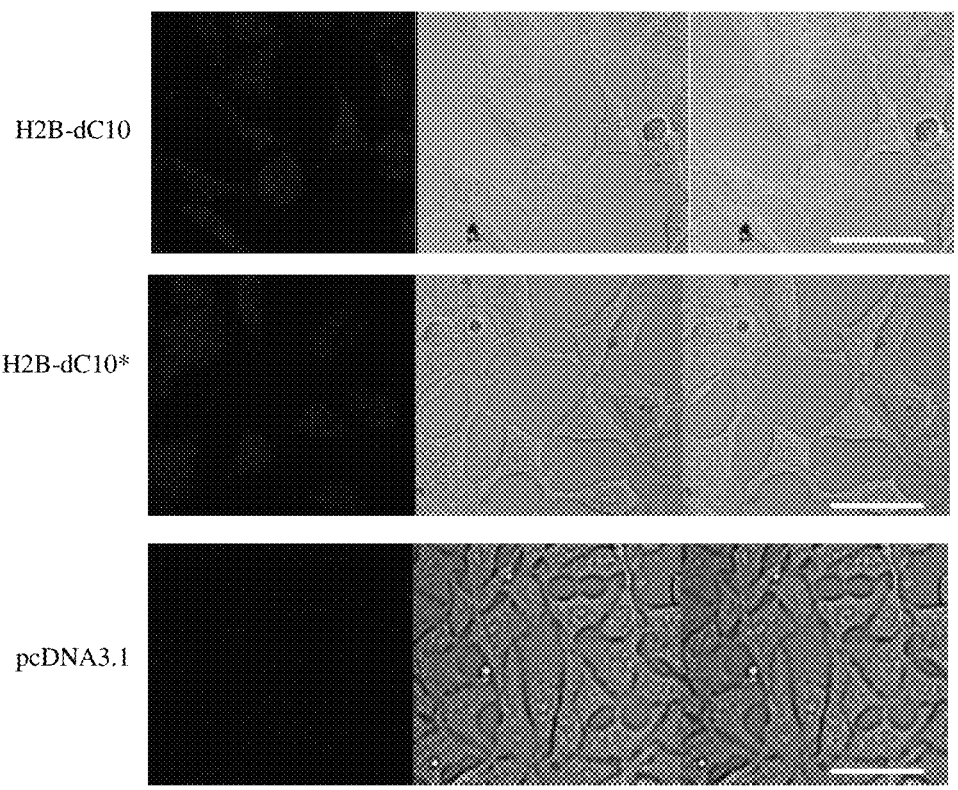
FIG. 14 shows H2B-dC10 and H2B-dC10* expressed in HEK293 cells and labelled with 10 μM of fluorogen 4. Cells transfected with plasmids coding for H2B-dC10, H2B-dC10* (dC10-A3KA16RA17K) and with an empty vector pcDNA3.1 were labelled with 10 μM of fluorogen 4 for 10 minutes and imaged by confocal microscopy (Em: 482 nm with 35 nm bandwidth, dichroic mirror 400-457 nm). Scale bar represents 50 μm.

Next we performed in cellulo labelling of H2B-dC10 and H2B-dC10* with fluorogen 4. The target sequences dC10 and dC10* (dC10-A3KA16RA17K) were cloned to the C-terminus of Histone-H2B, a cellular protein localized in the nuclei, as previously described (Chen, Y. et al., Angew. Chem. Int. Ed. Engl. 53: 13785-13788, 2014). Fluorogenic labelling agent 4 was chosen for an in cellulo labelling demonstration due to its excellent selectivity over glutathione, in comparison with methyl-disubstituted 3, or methyl/methoxy-substituted 2 (see Chen, Y. et al., Angew. Chem. Int. Ed. Engl. 53: 13785-13788, 2014). Both H2B-dC10 and H2B-dC10* were efficiently labelled with fluorogen 4, as shown in FIG. 14, where the coumarin cyan fluorescence is localized to the cell nuclei, corresponding to H2B localization. This clearly demonstrates the utility of the dC10* sequence for intracellular labelling of a protein of interest.

In conclusion, we have substantially improved a fluorogenic dimaleimide-based labelling technique through a rational design of a target peptide tag. At least one of these new tags, having the sequence 'LSKAECAAREAACRER-KARAGGK', reacts an order of magnitude faster than the parent dC10 tag. The new peptide tags can provide a much faster and/or more selective labelling of a POI inside a cell, where a fluorogenic labelling molecule can be exposed to a

TABLE 2

Second order rate constants for MBP-dC15 and MBP-dC10 measured with the indicated fluorogen at 20° C.

| Fluorogen | MBP-dC10 | MBP-dC15 |
|---|---|---|
| 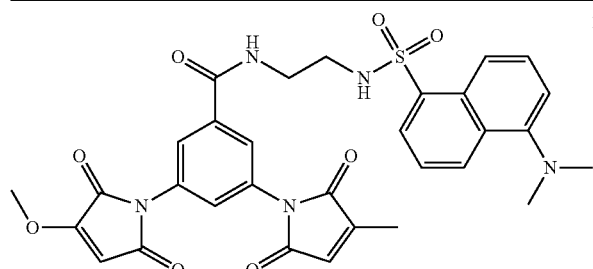 | $1640 M^{-1} min^{-1}$ | $761 M^{-1} min^{-1}$ |
| 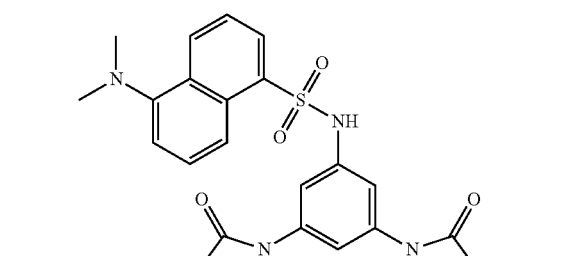 | $1150 M^{-1} min^{-1}$ | $2750 M^{-1} min^{-1}$ | large number of potentially reactive thiols. It is also noted that the presence of a higher number of charged residues on the new tag(s) may increase the overall solubility of the peptide tag.

Materials and Methods

Cloning of MBP-dC10 Single, Double and Triple Mutant Libraries.

All reagents and solvents for reactions were used as received unless otherwise stated. All cloning was performed using standard PCR amplification by KOD Xtreme™ Hot Start DNA polymerase (Millipore (Canada) Ltd., Etobicoke, Ontario, Canada) unless stated otherwise. DNA oligonucleotides were purchased from Integrated DNA Technologies, Inc. (Coralville, Iowa, United States), and all mutants were identified using Sanger sequencing at the Génome Québec Innovation Centre sequencing service (Montreal, Quebec, Canada; gqinnovationcenter.com).

The MBP-dC10 expression plasmid was created using the following approach: a 700 by 3' fragment of the malE gene from the pMAL-c5X vector (New England Biolabs, Ipswich, Mass., United States) was amplified by PCR using pMAL-fw primer (5'-CAAAGATCTGCTGCCG-3') and a reverse mega-primer containing a sequence annealing at the 3' end of the malE gene, the reverse coding sequence of the dC10 peptide tag, a stop codon and an EcoRI restriction site (5'-GGAATTCCCTACTTTCCTCCAGCTCTAGCTGCA-GCTTCTCTGCATGCAGCTTCT CTAGCAGCG-CACTCAGCAGCGCTCAGCCTTCCCTCGATCCC-3'). The resulting amplified fragment was inserted into the original pMAL-c5x vector using BglII and EcoRI restriction sites and correct clones were identified by restriction analysis and confirmed by sequencing.

A single mutant library I of MBP-dC10 at position A17 was created by site-directed mutagenesis using a degenerate codon VRN that allowed replacement of residue A17 by D, E, G, H, K, N, Q, R or S. Mutant MBP-dC10 A17G was identified but was not characterized further since only polar or positively charged residues at position A17 were desired in this study. A rolling circle PCR was performed with two primers (dC10_A17X_fw and dC10_A17X_bw) containing the mentioned VRN codon and its complementary codon (see Table 3).

A double mutant library II was created using mutant MBP-dC10 A17K as template, and DNA primers dC10-A16HR_A17K_fw and dC10-A16HR_A17K_bw containing a degenerate CRY codon for creation of double mutants MBP-dC10 A16H-A17K, and MBP-dC10 A16R-A17K (see Table 3). A pair of standard DNA primers MBP-dC10 A16K-A17K_fw and MBP-dC10 A16K-A17K_bw (see Table 3) was used to introduce the A16K-A17K mutation. As a control, double mutations R9K-A17H, R9K-A17K and R9K-A17R were prepared to investigate the importance of residue R9 whose side chain is thought to form an ionic bridge with nearby glutamate E5. Simple DNA primers dC10-R9K_fw and dC10-R9K_bw (see Table 3) were used for rolling circle PCR of parent MBP-dC10 A17H, A17K or A17R plasmids.

A triple mutant library III on position A3 was created from previously identified double mutants MBP-dC10 A16H-A17K, MBP-dC10 A16K-A17K and MBP-dC10 A16R-A17K. A degenerate codon CRY was used for introduction of residues H or R on position A3 (see Table 3) and a pair of standard oligonucleotides was used for A3K mutagenesis (see Table 3). Triple mutants A3R-A16K-A17K and A3H-A16R-A17K were prepared slightly differently: A new pair of oligonucleotides (dC10_A3R_fw and dC10_A3R_bw) was used to introduce the A3R mutation in MBP-dC10 A16K-A17K by rolling-circle PCR; and a site-overlap extension PCR using VentR® DNA Polymerase (New England Biolabs, Ipswich, Mass., United States) and primers A3H_fw and A3H_bw (see Table 3) was used to amplify the mutated portion of A3H-A16R-A17K that was subsequently inserted into the parent pMAL-c5x vector between the BglII and EcoRI restriction sites.

Expression and Purification of MBP-dC10 Variants.

All mutants of MBP-dC10 were expressed in BL21 (DE3) Gold strain of E. coli and purified in high yields. Transformed cells were grown in 250-350 mL of LB media supplemented with 0.2% D-glucose and 100 µM ampicillin. Expression of recombinant MBP-dC10 (or its variants) was induced with 0.3 mM IPTG at OD ~0.6, and was carried out at 37° C. for 3-4 hours with vigorous shaking. Cells were harvested by centrifugation at 4000 g for 15 minutes, resuspended in 10 mL of MBP-binding buffer (Tris 20 mM pH 7.4, NaCl 200 mM, EDTA 1 mM) and stored at −20° C.

Thawed cells were lysed by sonication on ice for 2×1 minute, and a soluble fraction was separated from insoluble proteins by centrifugation at 6000 g for 15 minutes at 4° C. The supernatant was loaded on amylose columns pre-equilibrated in MBP-binding buffer, and incubated at 4° C. with gentle stirring for 2 hours. Unbound proteins were washed from the column with 5 mL of MBP-binding buffer, and pure MBP-dC10 (or variants) was eluted by 3 mL of MBP-binding buffer containing 10 mM of maltose. An overnight dialysis was performed into HEPES 50 mM pH 7.5, TCEP 1 mM before kinetic characterization of MBP-dC10 variants. According to a Bradford assay, a high yield of 5-15 mg of each protein after purification was obtained using this protocol.

Kinetic Characterization of MBP-dC10 Variants by Fluorogenic Reaction with dM10 Fluorogens.

Figure 11:
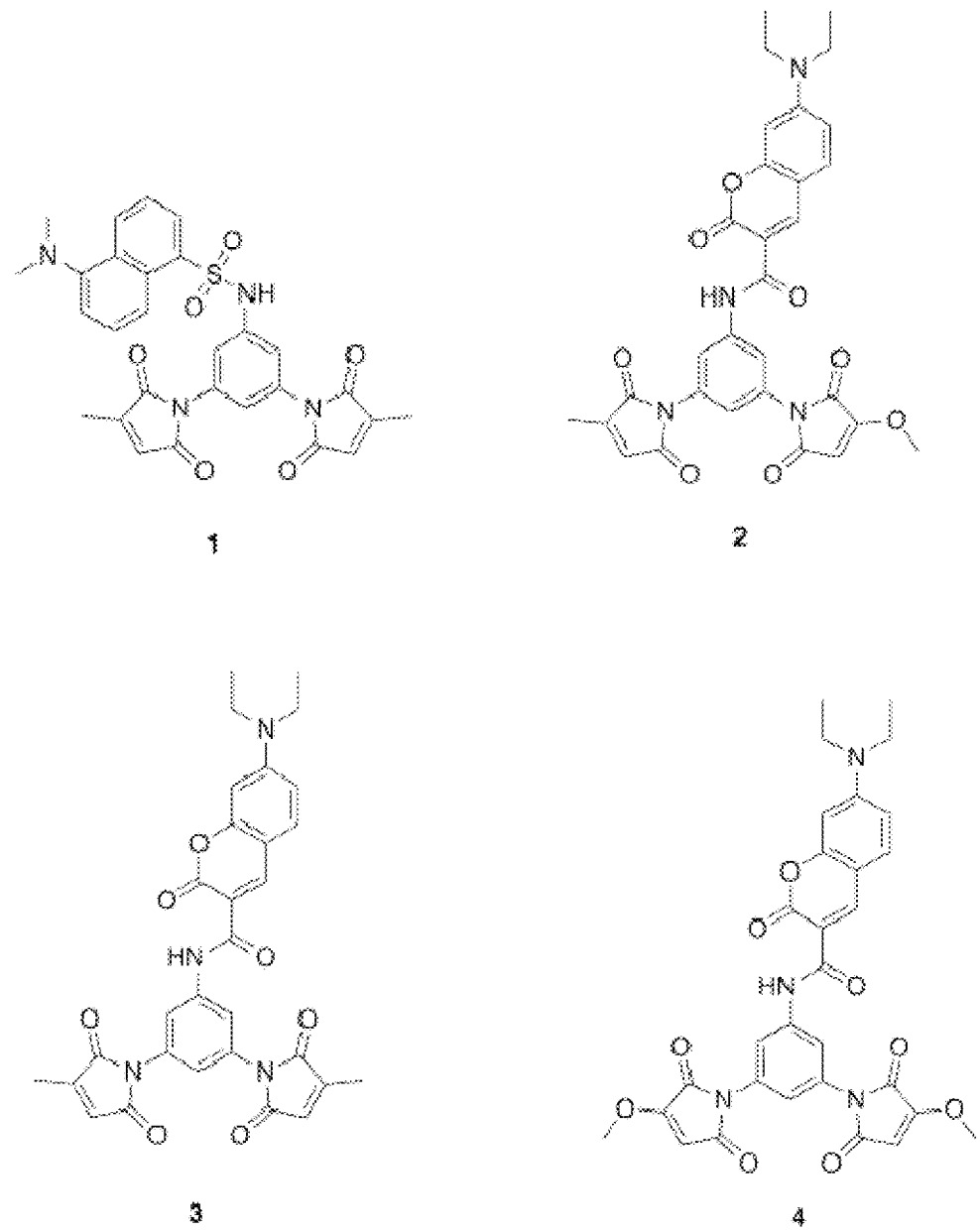
FIG. 11 shows the structures of fluorogens 1 (dansyl-dimaleimide; on top left), 2 (coumarin-dimaleimide; on top right), 3 (on bottom left), and 4 (on bottom right), used for in vitro kinetics.

Reactivity of each MBP-dC10 variant was assessed by determining the second order rate constant of the fluorogenic labelling reaction with a dansyl-dimaleimide fluorogenic molecule, referred to as dansyl-dM10 1 (FIG. 11). Dansyl-dM10 was synthesized as described (Caron, K. et al., Org. Biomol. Chem. 9: 185-197, 2011). Initial kinetic studies performed on MBP-dC10 histidine mutants S2H, R9H, A7H and S2H-A17H were done at the scale of 500 µL in the established conditions described below, using a Cary Eclipse Fluorimeter (Varian, Inc., Mississauga, Ontario, Canada) at 20° C. Reaction temperature was adjusted to 28° C. only for latter experiments where a plate reader that does not allow sample cooling was used.

Libraries I, II and III were assayed using a plate reader: briefly, in a reaction scale of 200 µL, 50 µM MBP-dC10 (or variants) and 50 µM dansyl-dM10 1 were mixed in HEPES 50 mM pH 7.5 buffer in the presence of TCEP 1 mM. Fluorescence increase was followed at 28° C. long after completion of the reaction (2 hours) using the Synergy™ H4 Hybrid Multi-Mode Microplate Reader (BioTek, Winooski, Vt., United States) plate reader at 515 nm, upon excitation at 330 nm of the dansyl fluorophore of 1. Second order reaction constants were determined using the initial slope and the final plateau of each kinetic curve. All reactions were performed in duplicate to quadruplicate. For pH dependent kinetics, MBP-dC10 variants were dialysed into a buffer of desired pH, containing 50 mM of buffering salt (pH 7.50-8.00: HEPES; pH 8.25-8.75: Tris-HCl; pH 9.00: CHES) and 1 mM TCEP, overnight at 4° C., with gentle stirring. Fluorogenic reactions were performed in a plate reader as described above, in duplicate.

In the case of labelling of MBP-dC10 and its variants with a coumarin dimaleimide derivative 2 (FIG. 11), a Cary Eclipse Fluorimeter was used. Under the same reaction conditions, fluorescence increase was followed at 28° C. at 485 nm upon excitation at 450 nm. Rate constants were determined by fitting to a second order equation using the Eclipse Kinetics software (Agilent Technologies, Santa Clara, Calif., United States). All reactions were performed in duplicate.

Prediction of Peptide Helicity Content.

An online version of AGADIR software (http://agadir.crg.es/; Munoz, V. and Serrano, L., Nat. Struct. Biol., 1:399-409 (1994)) was used for prediction of dC10 peptide helicity in the pH range of 7.50-9.10, at 301 K and an ionic strength of 0.1 M.

TABLE 3

Oligonucleotides used in methods described herein.

| Name | DNA Sequence (5' → 3')* | SEQ ID NO. |
|---|---|---|
| dC10-A17X_fw | GCAGAGAAGCTVRNGCTAGAGCTGGAGGAAAGTAGGGAATTCC | 44 |
| dC10-A17X_bw | CCTCCAGCTCTAGCNYBAGCTTCTCTGCATGCAGCTTCTCTAGC | 45 |
| dC10-R9K_fw | GCTGCTGAGTGCGCTGCTAAAGAAGCTGCATGCAGAGAAGC | 46 |
| dC10-R9K_bw | CATGCAGCTTCTTTAGCAGCGCACTCAGCAGCGCTCAGCCTTCC | 47 |
| dC10-A16HR-A17K_fw | GCAGAGAACRYAAAGCTAGAGCTGGAGGAAAGTAGGGAATTCC | 48 |
| dC10-A16HR-A17K_bw | CCTCCAGCTCTAGCTTTRYGTTCTCTGCATGCAGCTTCTCTAGC | 49 |
| dC10-A16K-A17K_fw | GCAGAGAAAAGAAAGCTAGAGCTGGAGGAAAGTAGGGAATTCC | 50 |
| dC10-A16K-A17K_bw | CCTCCAGCTCTAGCTTTCTTTTCTCTGCATGCAGCTTCTCTAGC | 51 |
| dC10-A3HR_fw | GAGGGAAGGCTGAGCCRYGCTGAGTGCGCTGCTAGAGAAG | 52 |
| dC10-A3HR_bw | CAGCGCACTCAGCRYGGCTCAGCCTTCCCTCGATCCCGAG | 53 |
| dC10-A3K_fw | GAGGGAAGGCTGAGCAAAGCTGAGTGCGCTGCTAGAGAAG | 54 |
| dC10-A3K_bw | CAGCGCACTCAGCTTTGCTCAGCCTTCCCTCGATCCCGAG | 55 |
| dC10-A3R_fw | GAGGGAAGGCTGAGCAGAGCTGAGTGCGCTGCTAGAGAAGCTG | 56 |
| dC10-A3R_bw | CAGCGCACTCAGCTCTGCTCAGCCTTCCCTCGATCCCGAG | 57 |
| dC10-A3H_fw | GAGGGAAGGCTGAGCCATGCTGAGTGCGCTGCTAGAGAAGCTG | 58 |
| dC10-A3H_bw | CAGCGCACTCAGCATGGCTCAGCCTTCCCTCGATCCCGAG | 59 |

*mutated codons are underlined

Although this invention is described in detail with reference to embodiments thereof, these embodiments are offered to illustrate but not to limit the invention. It is possible to make other embodiments that employ the principles of the invention and that fall within its spirit and scope as defined by the claims appended hereto.

The contents of all documents and references cited herein are hereby incorporated by reference in their entirety.

What is claimed is:

1. A peptide comprising the amino acid sequence set forth in SEQ ID NO. 2:

$L_1SX_3AECAAX_9EAACREX_{16}X_{17}ARAGGK_{23}$ (SEQ ID NO: 2)

wherein:
- $X_3$ and $X_{16}$ are independently selected from the group consisting of A, R, K, and H;
- $X_9$ is R; and
- $X_{17}$ is A, D, E, H, K, R, N, Q, or S;

except that at least one of $X_3$, $X_{16}$, and $X_{17}$ is not A, and when $X_{17}$ is H, either $X_3$ is not A or $X_{16}$ is not A; or SEQ ID NO: 2 as defined above, further comprising one or two amino acid substitution(s), wherein the substitution(s) retain binding to a dimaleimide fluorescent labelling agent, wherein said substitution(s) are at position 1, 2, 4, 5, 7, 8, 10, 11, 12, 14, 15, 18, 19, 20, 21, 22, or 23 of SEQ ID NO: 2.

2. The peptide of claim 1, wherein $X_{17}$ is selected from the group consisting of A, R, K, and H.

3. The peptide of claim 1, wherein $X_3$ is K; $X_{16}$ is R; and $X_{17}$ is K.

4. The peptide of claim 1, wherein the peptide comprises the amino acid sequence selected from the group consisting of SEQ ID NOs: 4, 5, 7-17, and 32-43.

5. The peptide of claim 1, wherein the peptide consists of the amino acid sequence selected from the group consisting of SEQ ID NOs: 4, 5, 7-17, and 32-43.

6. The peptide of claim 1, wherein the peptide binds specifically to a dimaleimide fluorescent labelling agent and reacts at least about 1.5× faster, at least about 2.5× faster, at least about 5× faster, or about 10× faster with the dimaleimide fluorescent labelling agent than the dC10 peptide.

7. The peptide of claim 1, wherein the peptide is synthetic, isolated, or pure.

8. The peptide of claim 1, wherein the dimaleimide fluorescent labelling agent is

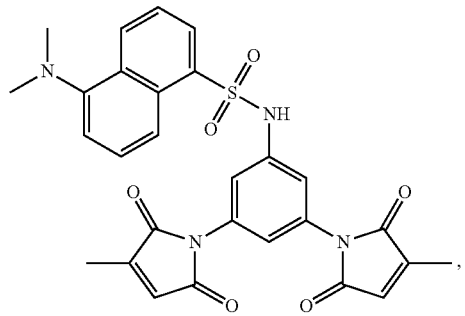

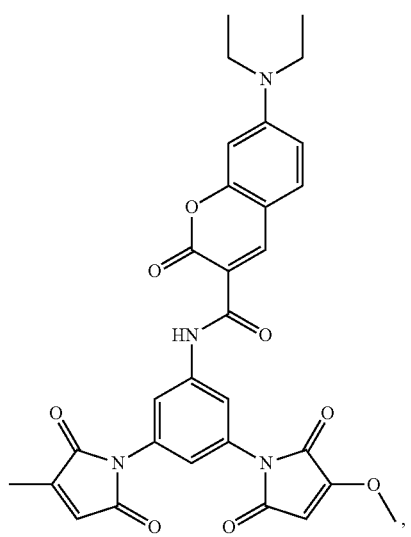

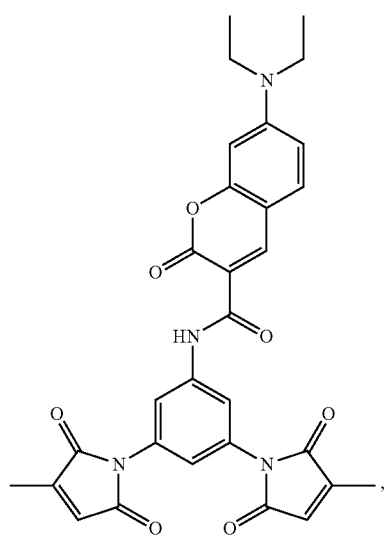

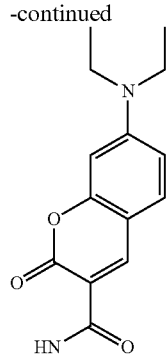

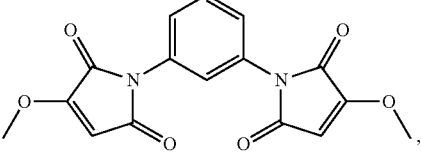

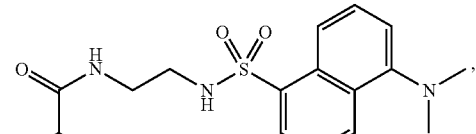

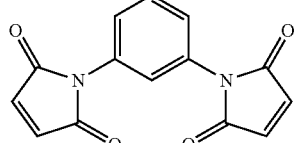

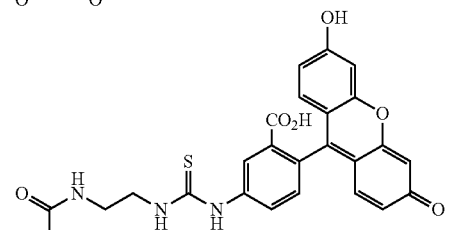

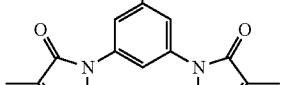

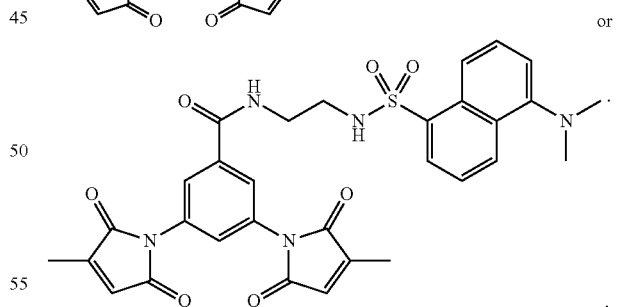

or

9. The peptide of claim 1, wherein:
(a) $X_3$ is A; $X_{16}$ is A; and $X_{17}$ is D, E, K, R, N, Q, or S;
(b) $X_3$ is A; $X_{16}$ is selected from A, R, K, and H; and $X_{17}$ is A, D, E, H, K, R, N, Q, or S, except that when $X_{17}$ is A or H, $X_{16}$ is not A;
(c) $X_3$ is A; $X_{17}$ is A; and $X_{16}$ is independently selected from R, K, and H;
(d) $X_3$ is A; $X_{16}$ is A; and $X_{17}$ is independently selected from R, K, and H;

(e) $X_{16}$ is A; and $X_3$ and $X_{17}$ are independently selected from A, R, K, and H, except that at least one of $X_3$ and $X_{17}$ is not A; or (f) $X_{17}$ is A; $X_3$ and $X_{16}$ are independently selected from A, R, K, and H, wherein at least one of $X_3$ and $X_{16}$ is not A.

10. A kit for labelling and/or detecting a target protein, the kit comprising the peptide of claim 1, or a nucleic acid encoding the peptide; and instructions for use thereof.

11. The kit of claim 10, wherein the kit further comprises a dimaleimide fluorescent labelling agent that reacts with said peptide.

12. A fusion protein comprising the peptide of claim 1 linked to a target protein.

13. An isolated or recombinant nucleic acid encoding the peptide of claim 1.

14. A vector comprising the nucleic acid of claim 13.

15. The vector of claim 14, wherein the vector is an expression vector or a cloning vector.

16. The vector of claim 14, wherein the vector further comprises a nucleic acid encoding a target protein.

17. A method for labelling and/or detecting a target protein, comprising:
    a) fusing the target protein to the peptide of claim 1;
    b) contacting the target protein with a dimaleimide fluorescent labelling agent under conditions where the dimaleimide fluorescent labelling agent reacts with the peptide fused to the target, wherein the fluorescence of the dimaleimide fluorescent labelling agent is quenched in the absence of reaction with the target protein; and
    c) upon reaction of the dimaleimide fluorescent labelling agent with the peptide fused to the target protein, detecting a fluorescent signal from the dimaleimide fluorescent labelling agent.

18. The method of claim 17, wherein the peptide is genetically fused to the target protein.

19. The method of claim 17, wherein the fluorescence of the dimaleimide fluorescent labelling agent increases after reaction with the target protein or is detectable only after reaction with the target protein.

20. The method of claim 17, wherein said contacting occurs in vivo, ex vivo, in vitro, or in a cultured cell expressing the target protein, wherein said target protein is an intracellular protein, an extracellular protein, or a cell-surface protein.

21. A method for live imaging of a target protein, comprising:
    a) fusing the target protein to the peptide of claim 1;
    b) contacting the target protein with a dimaleimide fluorescent labelling agent under conditions where the dimaleimide fluorescent labelling agent reacts with the peptide fused to the target protein, wherein the fluorescence of the dimaleimide fluorescent labelling agent is quenched in the absence of reaction with the target protein; and
    c) upon reaction of the dimaleimide fluorescent labelling agent with the peptide fused to the target protein, detecting a fluorescent signal from the dimaleimide fluorescent labelling agent.

* * * * *

SEQUENCE LISTING

<160> NUMBER OF SEQ ID NOS: 114

<210> SEQ ID NO 1
<211> LENGTH: 23
<212> TYPE: PRT
<213> ORGANISM: Artificial Sequence
<220> FEATURE:
<223> OTHER INFORMATION: synthesized

<400> SEQUENCE: 1

Leu Ser Ala Ala Glu Cys Ala Ala Arg Glu Ala Ala Cys Arg Glu Ala
1               5                   10                  15

Ala Ala Arg Ala Gly Gly Lys
            20

<210> SEQ ID NO 2
<211> LENGTH: 23
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid

<400> SEQUENCE: 2

Leu Ser Xaa Ala Glu Cys Ala Ala Xaa Glu Ala Ala Cys Arg Glu Xaa
1               5                   10                  15

Xaa Ala Arg Ala Gly Gly Lys
            20

<210> SEQ ID NO 3
<211> LENGTH: 23
<212> TYPE: PRT
<213> ORGANISM: Artificial Sequence
<220> FEATURE:
<223> OTHER INFORMATION: synthesized
<220> FEATURE:
<221> NAME/KEY: misc_feature
<222> LOCATION: (17)..(17)
<223> OTHER INFORMATION: Xaa can be any naturally occurring amino acid

<400> SEQUENCE: 3

Leu Ser Ala Ala Glu Cys Ala Ala Arg Glu Ala Ala Cys Arg Glu Ala
1               5                   10                  15

Xaa Ala Arg Ala Gly Gly Lys
            20

<210> SEQ ID NO 4
<211> LENGTH: 23
<212> TYPE: PRT
<213> ORGANISM: Artificial Sequence
<220> FEATURE:
<223> OTHER INFORMATION: synthesized -continued

```
<400> SEQUENCE: 4

Leu Ser Ala Ala Glu Cys Ala Ala Arg Glu Ala Ala Cys Arg Glu Ala
1               5                   10                  15

Asp Ala Arg Ala Gly Gly Lys
            20

<210> SEQ ID NO 5
<211> LENGTH: 23
<212> TYPE: PRT
<213> ORGANISM: Artificial Sequence
<220> FEATURE:
<223> OTHER INFORMATION: synthesized

<400> SEQUENCE: 5

Leu Ser Ala Ala Glu Cys Ala Ala Arg Glu Ala Ala Cys Arg Glu Ala
1               5                   10                  15

Glu Ala Arg Ala Gly Gly Lys
            20

<210> SEQ ID NO 6
<211> LENGTH: 23
<212> TYPE: PRT
<213> ORGANISM: Artificial Sequence
<220> FEATURE:
<223> OTHER INFORMATION: synthesized

<400> SEQUENCE: 6

Leu Ser Ala Ala Glu Cys Ala Ala Arg Glu Ala Ala Cys Arg Glu Ala
1               5                   10                  15

His Ala Arg Ala Gly Gly Lys
            20

<210> SEQ ID NO 7
<211> LENGTH: 23
<212> TYPE: PRT
<213> ORGANISM: Artificial Sequence
<220> FEATURE:
<223> OTHER INFORMATION: synthesized

<400> SEQUENCE: 7

Leu Ser Ala Ala Glu Cys Ala Ala Arg Glu Ala Ala Cys Arg Glu Ala
1               5                   10                  15

Lys Ala Arg Ala Gly Gly Lys
            20

<210> SEQ ID NO 8
<211> LENGTH: 23
<212> TYPE: PRT
<213> ORGANISM: Artificial Sequence
<220> FEATURE:
<223> OTHER INFORMATION: synthesized

<400> SEQUENCE: 8

Leu Ser Ala Ala Glu Cys Ala Ala Arg Glu Ala Ala Cys Arg Glu Ala
1               5                   10                  15

Asn Ala Arg Ala Gly Gly Lys
            20

<210> SEQ ID NO 9
<211> LENGTH: 23
<212> TYPE: PRT
<213> ORGANISM: Artificial Sequence
<220> FEATURE:
<223> OTHER INFORMATION: synthesized
```

-continued

```
<400> SEQUENCE: 9

Leu Ser Ala Ala Glu Cys Ala Ala Arg Glu Ala Ala Cys Arg Glu Ala
1               5                   10                  15

Gln Ala Arg Ala Gly Gly Lys
            20

<210> SEQ ID NO 10
<211> LENGTH: 23
<212> TYPE: PRT
<213> ORGANISM: Artificial Sequence
<220> FEATURE:
<223> OTHER INFORMATION: synthesized

<400> SEQUENCE: 10

Leu Ser Ala Ala Glu Cys Ala Ala Arg Glu Ala Ala Cys Arg Glu Ala
1               5                   10                  15

Arg Ala Arg Ala Gly Gly Lys
            20

<210> SEQ ID NO 11
<211> LENGTH: 23
<212> TYPE: PRT
<213> ORGANISM: Artificial Sequence
<220> FEATURE:
<223> OTHER INFORMATION: synthesized

<400> SEQUENCE: 11

Leu Ser Ala Ala Glu Cys Ala Ala Arg Glu Ala Ala Cys Arg Glu Ala
1               5                   10                  15

Ser Ala Arg Ala Gly Gly Lys
            20

<210> SEQ ID NO 12
<211> LENGTH: 23
<212> TYPE: PRT
<213> ORGANISM: Artificial Sequence
<220> FEATURE:
<223> OTHER INFORMATION: synthesized

<400> SEQUENCE: 12

Leu Ser Ala Ala Glu Cys Ala Ala Arg Glu Ala Ala Cys Arg Glu Lys
1               5                   10                  15

Ala Ala Arg Ala Gly Gly Lys
            20

<210> SEQ ID NO 13
<211> LENGTH: 23
<212> TYPE: PRT
<213> ORGANISM: Artificial Sequence
<220> FEATURE:
<223> OTHER INFORMATION: synthesized

<400> SEQUENCE: 13

Leu Ser Ala Ala Glu Cys Ala Ala Arg Glu Ala Ala Cys Arg Glu Arg
1               5                   10                  15

Ala Ala Arg Ala Gly Gly Lys
            20

<210> SEQ ID NO 14
<211> LENGTH: 23
<212> TYPE: PRT
<213> ORGANISM: Artificial Sequence
<220> FEATURE:
<223> OTHER INFORMATION: synthesized
```

<400> SEQUENCE: 14

Leu Ser Ala Ala Glu Cys Ala Ala Arg Glu Ala Ala Cys Arg Glu His
1               5                   10                  15

Ala Ala Arg Ala Gly Gly Lys
            20

<210> SEQ ID NO 15
<211> LENGTH: 23
<212> TYPE: PRT
<213> ORGANISM: Artificial Sequence
<220> FEATURE:
<223> OTHER INFORMATION: synthesized

<400> SEQUENCE: 15

Leu Ser Lys Ala Glu Cys Ala Ala Arg Glu Ala Ala Cys Arg Glu Ala
1               5                   10                  15

Ala Ala Arg Ala Gly Gly Lys
            20

<210> SEQ ID NO 16
<211> LENGTH: 23
<212> TYPE: PRT
<213> ORGANISM: Artificial Sequence
<220> FEATURE:
<223> OTHER INFORMATION: synthesized

<400> SEQUENCE: 16

Leu Ser Arg Ala Glu Cys Ala Ala Arg Glu Ala Ala Cys Arg Glu Ala
1               5                   10                  15

Ala Ala Arg Ala Gly Gly Lys
            20

<210> SEQ ID NO 17
<211> LENGTH: 23
<212> TYPE: PRT
<213> ORGANISM: Artificial Sequence
<220> FEATURE:
<223> OTHER INFORMATION: synthesized

<400> SEQUENCE: 17

Leu Ser His Ala Glu Cys Ala Ala Arg Glu Ala Ala Cys Arg Glu Ala
1               5                   10                  15

Ala Ala Arg Ala Gly Gly Lys
            20

<210> SEQ ID NO 18
<211> LENGTH: 23
<212> TYPE: PRT
<213> ORGANISM: Artificial Sequence
<220> FEATURE:
<223> OTHER INFORMATION: synthesized

<400> SEQUENCE: 18

Leu Ser Ala Ala Glu Cys Ala Ala Lys Glu Ala Ala Cys Arg Glu Ala
1               5                   10                  15

Ala Ala Arg Ala Gly Gly Lys
            20

<210> SEQ ID NO 19
<211> LENGTH: 23
<212> TYPE: PRT
<213> ORGANISM: Artificial Sequence
<220> FEATURE:
<223> OTHER INFORMATION: synthesized

```
<400> SEQUENCE: 19

Leu His Ala Ala Glu Cys Ala Ala Arg Glu Ala Ala Cys Arg Glu Ala
1               5                   10                  15

Ala Ala Arg Ala Gly Gly Lys
            20

<210> SEQ ID NO 20
<211> LENGTH: 23
<212> TYPE: PRT
<213> ORGANISM: Artificial Sequence
<220> FEATURE:
<223> OTHER INFORMATION: synthesized

<400> SEQUENCE: 20

Leu Ser Ala Ala Glu Cys His Ala Arg Glu Ala Ala Cys Arg Glu Ala
1               5                   10                  15

Ala Ala Arg Ala Gly Gly Lys
            20

<210> SEQ ID NO 21
<211> LENGTH: 23
<212> TYPE: PRT
<213> ORGANISM: Artificial Sequence
<220> FEATURE:
<223> OTHER INFORMATION: synthesized

<400> SEQUENCE: 21

Leu Ser Ala Ala Glu Cys Ala Ala His Glu Ala Ala Cys Arg Glu Ala
1               5                   10                  15

Ala Ala Arg Ala Gly Gly Lys
            20

<210> SEQ ID NO 22
<211> LENGTH: 23
<212> TYPE: PRT
<213> ORGANISM: Artificial Sequence
<220> FEATURE:
<223> OTHER INFORMATION: synthesized

<400> SEQUENCE: 22

Leu His Ala Ala Glu Cys Ala Ala Arg Glu Ala Ala Cys Arg Glu Ala
1               5                   10                  15

His Ala Arg Ala Gly Gly Lys
            20

<210> SEQ ID NO 23
<211> LENGTH: 23
<212> TYPE: PRT
<213> ORGANISM: Artificial Sequence
<220> FEATURE:
<223> OTHER INFORMATION: synthesized

<400> SEQUENCE: 23

Leu Ser Ala Ala Glu Cys Ala Ala Lys Glu Ala Ala Cys Arg Glu Ala
1               5                   10                  15

His Ala Arg Ala Gly Gly Lys
            20

<210> SEQ ID NO 24
<211> LENGTH: 23
<212> TYPE: PRT
<213> ORGANISM: Artificial Sequence
<220> FEATURE:
<223> OTHER INFORMATION: synthesized
```

-continued

```
<400> SEQUENCE: 24

Leu Ser Ala Ala Glu Cys Ala Ala Lys Glu Ala Ala Cys Arg Glu Ala
1               5                   10                  15

Lys Ala Arg Ala Gly Gly Lys
            20

<210> SEQ ID NO 25
<211> LENGTH: 23
<212> TYPE: PRT
<213> ORGANISM: Artificial Sequence
<220> FEATURE:
<223> OTHER INFORMATION: synthesized

<400> SEQUENCE: 25

Leu Ser Ala Ala Glu Cys Ala Ala Lys Glu Ala Ala Cys Arg Glu Ala
1               5                   10                  15

Arg Ala Arg Ala Gly Gly Lys
            20

<210> SEQ ID NO 26
<211> LENGTH: 23
<212> TYPE: PRT
<213> ORGANISM: Artificial Sequence
<220> FEATURE:
<223> OTHER INFORMATION: synthesized

<400> SEQUENCE: 26

Leu Ser Ala Ala Glu Cys Ala Ala His Glu Ala Ala Cys Arg Glu Ala
1               5                   10                  15

His Ala Arg Ala Gly Gly Lys
            20

<210> SEQ ID NO 27
<211> LENGTH: 23
<212> TYPE: PRT
<213> ORGANISM: Artificial Sequence
<220> FEATURE:
<223> OTHER INFORMATION: synthesized

<400> SEQUENCE: 27

Leu Ser Ala Ala Glu Cys Ala Ala His Glu Ala Ala Cys Arg Glu Ala
1               5                   10                  15

Lys Ala Arg Ala Gly Gly Lys
            20

<210> SEQ ID NO 28
<211> LENGTH: 23
<212> TYPE: PRT
<213> ORGANISM: Artificial Sequence
<220> FEATURE:
<223> OTHER INFORMATION: synthesized

<400> SEQUENCE: 28

Leu Ser Ala Ala Glu Cys Ala Ala His Glu Ala Ala Cys Arg Glu Ala
1               5                   10                  15

Arg Ala Arg Ala Gly Gly Lys
            20

<210> SEQ ID NO 29
<211> LENGTH: 23
<212> TYPE: PRT
<213> ORGANISM: Artificial Sequence
<220> FEATURE:
<223> OTHER INFORMATION: synthesized
```

```
<400> SEQUENCE: 29

Leu Ser Ala Ala Glu Cys Ala Ala Lys Glu Ala Ala Cys Arg Glu His
1               5                   10                  15

Ala Ala Arg Ala Gly Gly Lys
            20

<210> SEQ ID NO 30
<211> LENGTH: 23
<212> TYPE: PRT
<213> ORGANISM: Artificial Sequence
<220> FEATURE:
<223> OTHER INFORMATION: synthesized

<400> SEQUENCE: 30

Leu Ser Ala Ala Glu Cys Ala Ala Lys Glu Ala Ala Cys Arg Glu Lys
1               5                   10                  15

Ala Ala Arg Ala Gly Gly Lys
            20

<210> SEQ ID NO 31
<211> LENGTH: 23
<212> TYPE: PRT
<213> ORGANISM: Artificial Sequence
<220> FEATURE:
<223> OTHER INFORMATION: synthesized

<400> SEQUENCE: 31

Leu Ser Ala Ala Glu Cys Ala Ala Lys Glu Ala Ala Cys Arg Glu Arg
1               5                   10                  15

Ala Ala Arg Ala Gly Gly Lys
            20

<210> SEQ ID NO 32
<211> LENGTH: 23
<212> TYPE: PRT
<213> ORGANISM: Artificial Sequence
<220> FEATURE:
<223> OTHER INFORMATION: synthesized

<400> SEQUENCE: 32

Leu Ser Ala Ala Glu Cys Ala Ala Arg Glu Ala Ala Cys Arg Glu His
1               5                   10                  15

Lys Ala Arg Ala Gly Gly Lys
            20

<210> SEQ ID NO 33
<211> LENGTH: 23
<212> TYPE: PRT
<213> ORGANISM: Artificial Sequence
<220> FEATURE:
<223> OTHER INFORMATION: synthesized

<400> SEQUENCE: 33

Leu Ser Ala Ala Glu Cys Ala Ala Arg Glu Ala Ala Cys Arg Glu Lys
1               5                   10                  15

Lys Ala Arg Ala Gly Gly Lys
            20

<210> SEQ ID NO 34
<211> LENGTH: 23
<212> TYPE: PRT
<213> ORGANISM: Artificial Sequence
<220> FEATURE:
<223> OTHER INFORMATION: synthesized
```

```
<400> SEQUENCE: 34

Leu Ser Ala Ala Glu Cys Ala Ala Arg Glu Ala Ala Cys Arg Glu Arg
1               5                   10                  15

Lys Ala Arg Ala Gly Gly Lys
            20

<210> SEQ ID NO 35
<211> LENGTH: 23
<212> TYPE: PRT
<213> ORGANISM: Artificial Sequence
<220> FEATURE:
<223> OTHER INFORMATION: synthesized

<400> SEQUENCE: 35

Leu Ser His Ala Glu Cys Ala Ala Arg Glu Ala Ala Cys Arg Glu His
1               5                   10                  15

Lys Ala Arg Ala Gly Gly Lys
            20

<210> SEQ ID NO 36
<211> LENGTH: 23
<212> TYPE: PRT
<213> ORGANISM: Artificial Sequence
<220> FEATURE:
<223> OTHER INFORMATION: synthesized

<400> SEQUENCE: 36

Leu Ser Lys Ala Glu Cys Ala Ala Arg Glu Ala Ala Cys Arg Glu His
1               5                   10                  15

Lys Ala Arg Ala Gly Gly Lys
            20

<210> SEQ ID NO 37
<211> LENGTH: 23
<212> TYPE: PRT
<213> ORGANISM: Artificial Sequence
<220> FEATURE:
<223> OTHER INFORMATION: synthesized

<400> SEQUENCE: 37

Leu Ser Arg Ala Glu Cys Ala Ala Arg Glu Ala Ala Cys Arg Glu His
1               5                   10                  15

Lys Ala Arg Ala Gly Gly Lys
            20

<210> SEQ ID NO 38
<211> LENGTH: 23
<212> TYPE: PRT
<213> ORGANISM: Artificial Sequence
<220> FEATURE:
<223> OTHER INFORMATION: synthesized

<400> SEQUENCE: 38

Leu Ser His Ala Glu Cys Ala Ala Arg Glu Ala Ala Cys Arg Glu Lys
1               5                   10                  15

Lys Ala Arg Ala Gly Gly Lys
            20

<210> SEQ ID NO 39
<211> LENGTH: 23
<212> TYPE: PRT
<213> ORGANISM: Artificial Sequence
<220> FEATURE:
<223> OTHER INFORMATION: synthesized
```

-continued

```
<400> SEQUENCE: 39

Leu Ser Lys Ala Glu Cys Ala Ala Arg Glu Ala Ala Cys Arg Glu Lys
1               5                   10                  15

Lys Ala Arg Ala Gly Gly Lys
            20

<210> SEQ ID NO 40
<211> LENGTH: 23
<212> TYPE: PRT
<213> ORGANISM: Artificial Sequence
<220> FEATURE:
<223> OTHER INFORMATION: synthesized

<400> SEQUENCE: 40

Leu Ser Arg Ala Glu Cys Ala Ala Arg Glu Ala Ala Cys Arg Glu Lys
1               5                   10                  15

Lys Ala Arg Ala Gly Gly Lys
            20

<210> SEQ ID NO 41
<211> LENGTH: 23
<212> TYPE: PRT
<213> ORGANISM: Artificial Sequence
<220> FEATURE:
<223> OTHER INFORMATION: synthesized

<400> SEQUENCE: 41

Leu Ser His Ala Glu Cys Ala Ala Arg Glu Ala Ala Cys Arg Glu Arg
1               5                   10                  15

Lys Ala Arg Ala Gly Gly Lys
            20

<210> SEQ ID NO 42
<211> LENGTH: 23
<212> TYPE: PRT
<213> ORGANISM: Artificial Sequence
<220> FEATURE:
<223> OTHER INFORMATION: synthesized

<400> SEQUENCE: 42

Leu Ser Lys Ala Glu Cys Ala Ala Arg Glu Ala Ala Cys Arg Glu Arg
1               5                   10                  15

Lys Ala Arg Ala Gly Gly Lys
            20

<210> SEQ ID NO 43
<211> LENGTH: 23
<212> TYPE: PRT
<213> ORGANISM: Artificial Sequence
<220> FEATURE:
<223> OTHER INFORMATION: synthesized

<400> SEQUENCE: 43

Leu Ser Arg Ala Glu Cys Ala Ala Arg Glu Ala Ala Cys Arg Glu Arg
1               5                   10                  15

Lys Ala Arg Ala Gly Gly Lys
            20

<210> SEQ ID NO 44
<211> LENGTH: 43
<212> TYPE: DNA
<213> ORGANISM: Artificial Sequence
<220> FEATURE:
<223> OTHER INFORMATION: synthesized
```

```
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 44
gcagagaagc tnnngctaga gctggaggaa agtagggaat tcc                43

<210> SEQ ID NO 45
<211> LENGTH: 44
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 45
cctccagctc tagcnnnagc ttctctgcat gcagcttctc tagc               44

<210> SEQ ID NO 46
<211> LENGTH: 41
<212> TYPE: DNA
<213> ORGANISM: Artificial Sequence
<220> FEATURE:
<223> OTHER INFORMATION: synthesized

<400> SEQUENCE: 46
gctgctgagt gcgctgctaa agaagctgca tgcagagaag c                  41

<210> SEQ ID NO 47
<211> LENGTH: 44
<212> TYPE: DNA
<213> ORGANISM: Artificial Sequence
<220> FEATURE:
<223> OTHER INFORMATION: synthesized

<400> SEQUENCE: 47
catgcagctt ctttagcagc gcactcagca gcgctcagcc ttcc               44

<210> SEQ ID NO 48
<211> LENGTH: 43
<212> TYPE: DNA
<213> ORGANISM: Artificial Sequence
<220> FEATURE:
<223> OTHER INFORMATION: synthesized

<400> SEQUENCE: 48
gcagagaacr yaaagctaga gctggaggaa agtagggaat tcc                43
```

```
<210> SEQ ID NO 49
<211> LENGTH: 44
<212> TYPE: DNA
<213> ORGANISM: Artificial Sequence
<220> FEATURE:
<223> OTHER INFORMATION: synthesized

<400> SEQUENCE: 49
cctccagctc tagctttryg ttctctgcat gcagcttctc tagc             44

<210> SEQ ID NO 50
<211> LENGTH: 43
<212> TYPE: DNA
<213> ORGANISM: Artificial Sequence
<220> FEATURE:
<223> OTHER INFORMATION: synthesized

<400> SEQUENCE: 50
gcagagaaaa gaaagctaga gctggaggaa agtagggaat tcc              43

<210> SEQ ID NO 51
<211> LENGTH: 44
<212> TYPE: DNA
<213> ORGANISM: Artificial Sequence
<220> FEATURE:
<223> OTHER INFORMATION: synthesized

<400> SEQUENCE: 51
cctccagctc tagctttctt ttctctgcat gcagcttctc tagc             44

<210> SEQ ID NO 52
<211> LENGTH: 40
<212> TYPE: DNA
<213> ORGANISM: Artificial Sequence
<220> FEATURE:
<223> OTHER INFORMATION: synthesized

<400> SEQUENCE: 52
gagggaaggc tgagccrygc tgagtgcgct gctagagaag                  40

<210> SEQ ID NO 53
<211> LENGTH: 40
<212> TYPE: DNA
<213> ORGANISM: Artificial Sequence
<220> FEATURE:
<223> OTHER INFORMATION: synthesized

<400> SEQUENCE: 53
cagcgcactc agcryggctc agccttccct cgatcccgag                  40

<210> SEQ ID NO 54
<211> LENGTH: 40
<212> TYPE: DNA
<213> ORGANISM: Artificial Sequence
<220> FEATURE:
<223> OTHER INFORMATION: synthesized

<400> SEQUENCE: 54
gagggaaggc tgagcaaagc tgagtgcgct gctagagaag                  40

<210> SEQ ID NO 55
<211> LENGTH: 40
<212> TYPE: DNA
<213> ORGANISM: Artificial Sequence
<220> FEATURE:
<223> OTHER INFORMATION: synthesized
```

<400> SEQUENCE: 55
cagcgcactc agctttgctc agccttccct cgatcccgag                                40

<210> SEQ ID NO 56
<211> LENGTH: 43
<212> TYPE: DNA
<213> ORGANISM: Artificial Sequence
<220> FEATURE:
<223> OTHER INFORMATION: synthesized

<400> SEQUENCE: 56
gagggaaggc tgagcagagc tgagtgcgct gctagagaag ctg                           43

<210> SEQ ID NO 57
<211> LENGTH: 40
<212> TYPE: DNA
<213> ORGANISM: Artificial Sequence
<220> FEATURE:
<223> OTHER INFORMATION: synthesized

<400> SEQUENCE: 57
cagcgcactc agctctgctc agccttccct cgatcccgag                                40

<210> SEQ ID NO 58
<211> LENGTH: 43
<212> TYPE: DNA
<213> ORGANISM: Artificial Sequence
<220> FEATURE:
<223> OTHER INFORMATION: synthesized

<400> SEQUENCE: 58
gagggaaggc tgagccatgc tgagtgcgct gctagagaag ctg                           43

<210> SEQ ID NO 59
<211> LENGTH: 40
<212> TYPE: DNA
<213> ORGANISM: Artificial Sequence
<220> FEATURE:
<223> OTHER INFORMATION: synthesized

<400> SEQUENCE: 59
cagcgcactc agcatggctc agccttccct cgatcccgag                                40

<210> SEQ ID NO 60
<211> LENGTH: 23
<212> TYPE: PRT
<213> ORGANISM: Artificial Sequence
<220> FEATURE:
<223> OTHER INFORMATION: synthesized

<400> SEQUENCE: 60

Leu Ser Ala Ala Glu Ala Cys Ala Arg Glu Ala Ala Arg Glu Ala
1               5                   10                  15

Ala Cys Arg Ala Gly Gly Lys
            20

<210> SEQ ID NO 61
<211> LENGTH: 23
<212> TYPE: PRT
<213> ORGANISM: Artificial Sequence
<220> FEATURE:
<223> OTHER INFORMATION: synthesized

```
<400> SEQUENCE: 61

Leu Ser Ala Ala Glu Ala Cys Ala Arg Glu His Ala Ala Arg Glu Ala
1               5                   10                  15

Ala Cys Arg Ala Gly Gly Lys
            20

<210> SEQ ID NO 62
<211> LENGTH: 23
<212> TYPE: PRT
<213> ORGANISM: Artificial Sequence
<220> FEATURE:
<223> OTHER INFORMATION: synthesized

<400> SEQUENCE: 62

Leu Ser Ala Ala Glu Ala Cys Ala Arg Glu Arg Ala Ala Arg Glu Ala
1               5                   10                  15

Ala Cys Arg Ala Gly Gly Lys
            20

<210> SEQ ID NO 63
<211> LENGTH: 23
<212> TYPE: PRT
<213> ORGANISM: Artificial Sequence
<220> FEATURE:
<223> OTHER INFORMATION: synthesized

<400> SEQUENCE: 63

Leu Ser Ala Ala Glu Ala Cys Ala Arg Glu Lys Ala Ala Arg Glu Ala
1               5                   10                  15

Ala Cys Arg Ala Gly Gly Lys
            20

<210> SEQ ID NO 64
<211> LENGTH: 23
<212> TYPE: PRT
<213> ORGANISM: Artificial Sequence
<220> FEATURE:
<223> OTHER INFORMATION: synthesized

<400> SEQUENCE: 64

Leu Ser Ala His Glu Ala Cys Ala Arg Glu Ala Ala Ala Arg Glu Ala
1               5                   10                  15

Ala Cys Arg Ala Gly Gly Lys
            20

<210> SEQ ID NO 65
<211> LENGTH: 23
<212> TYPE: PRT
<213> ORGANISM: Artificial Sequence
<220> FEATURE:
<223> OTHER INFORMATION: synthesized

<400> SEQUENCE: 65

Leu Ser Ala Arg Glu Ala Cys Ala Arg Glu Ala Ala Ala Arg Glu Ala
1               5                   10                  15

Ala Cys Arg Ala Gly Gly Lys
            20

<210> SEQ ID NO 66
<211> LENGTH: 23
<212> TYPE: PRT
<213> ORGANISM: Artificial Sequence
<220> FEATURE:
<223> OTHER INFORMATION: synthesized
```

```
<400> SEQUENCE: 66

Leu Ser Ala Lys Glu Ala Cys Ala Arg Glu Ala Ala Ala Arg Glu Ala
1               5                   10                  15

Ala Cys Arg Ala Gly Gly Lys
            20

<210> SEQ ID NO 67
<211> LENGTH: 23
<212> TYPE: PRT
<213> ORGANISM: Artificial Sequence
<220> FEATURE:
<223> OTHER INFORMATION: synthesized

<400> SEQUENCE: 67

Leu Ser His Ala Glu Ala Cys Ala Arg Glu Ala Ala Ala Arg Glu Ala
1               5                   10                  15

Ala Cys Arg Ala Gly Gly Lys
            20

<210> SEQ ID NO 68
<211> LENGTH: 23
<212> TYPE: PRT
<213> ORGANISM: Artificial Sequence
<220> FEATURE:
<223> OTHER INFORMATION: synthesized

<400> SEQUENCE: 68

Leu Ser Arg Ala Glu Ala Cys Ala Arg Glu Ala Ala Ala Arg Glu Ala
1               5                   10                  15

Ala Cys Arg Ala Gly Gly Lys
            20

<210> SEQ ID NO 69
<211> LENGTH: 23
<212> TYPE: PRT
<213> ORGANISM: Artificial Sequence
<220> FEATURE:
<223> OTHER INFORMATION: synthesized

<400> SEQUENCE: 69

Leu Ser Lys Ala Glu Ala Cys Ala Arg Glu Ala Ala Ala Arg Glu Ala
1               5                   10                  15

Ala Cys Arg Ala Gly Gly Lys
            20

<210> SEQ ID NO 70
<211> LENGTH: 23
<212> TYPE: PRT
<213> ORGANISM: Artificial Sequence
<220> FEATURE:
<223> OTHER INFORMATION: synthesized

<400> SEQUENCE: 70

Leu Ser Ala His Glu Ala Cys Ala Arg Glu His Ala Ala Arg Glu Ala
1               5                   10                  15

Ala Cys Arg Ala Gly Gly Lys
            20

<210> SEQ ID NO 71
<211> LENGTH: 23
<212> TYPE: PRT
<213> ORGANISM: Artificial Sequence
<220> FEATURE:
<223> OTHER INFORMATION: synthesized
```

-continued

```
<400> SEQUENCE: 71

Leu Ser Ala Arg Glu Ala Cys Ala Arg Glu His Ala Ala Arg Glu Ala
1               5                   10                  15

Ala Cys Arg Ala Gly Gly Lys
            20

<210> SEQ ID NO 72
<211> LENGTH: 23
<212> TYPE: PRT
<213> ORGANISM: Artificial Sequence
<220> FEATURE:
<223> OTHER INFORMATION: synthesized

<400> SEQUENCE: 72

Leu Ser Ala Lys Glu Ala Cys Ala Arg Glu His Ala Ala Arg Glu Ala
1               5                   10                  15

Ala Cys Arg Ala Gly Gly Lys
            20

<210> SEQ ID NO 73
<211> LENGTH: 23
<212> TYPE: PRT
<213> ORGANISM: Artificial Sequence
<220> FEATURE:
<223> OTHER INFORMATION: synthesized

<400> SEQUENCE: 73

Leu Ser Ala His Glu Ala Cys Ala Arg Glu Arg Ala Ala Arg Glu Ala
1               5                   10                  15

Ala Cys Arg Ala Gly Gly Lys
            20

<210> SEQ ID NO 74
<211> LENGTH: 23
<212> TYPE: PRT
<213> ORGANISM: Artificial Sequence
<220> FEATURE:
<223> OTHER INFORMATION: synthesized

<400> SEQUENCE: 74

Leu Ser Ala Arg Glu Ala Cys Ala Arg Glu Arg Ala Ala Arg Glu Ala
1               5                   10                  15

Ala Cys Arg Ala Gly Gly Lys
            20

<210> SEQ ID NO 75
<211> LENGTH: 23
<212> TYPE: PRT
<213> ORGANISM: Artificial Sequence
<220> FEATURE:
<223> OTHER INFORMATION: synthesized

<400> SEQUENCE: 75

Leu Ser Ala Lys Glu Ala Cys Ala Arg Glu Arg Ala Ala Arg Glu Ala
1               5                   10                  15

Ala Cys Arg Ala Gly Gly Lys
            20

<210> SEQ ID NO 76
<211> LENGTH: 23
<212> TYPE: PRT
<213> ORGANISM: Artificial Sequence
<220> FEATURE:
<223> OTHER INFORMATION: synthesized
```

```
<400> SEQUENCE: 76

Leu Ser Ala His Glu Ala Cys Ala Arg Glu Lys Ala Ala Arg Glu Ala
1               5                   10                  15

Ala Cys Arg Ala Gly Gly Lys
            20

<210> SEQ ID NO 77
<211> LENGTH: 23
<212> TYPE: PRT
<213> ORGANISM: Artificial Sequence
<220> FEATURE:
<223> OTHER INFORMATION: synthesized

<400> SEQUENCE: 77

Leu Ser Ala Arg Glu Ala Cys Ala Arg Glu Lys Ala Ala Arg Glu Ala
1               5                   10                  15

Ala Cys Arg Ala Gly Gly Lys
            20

<210> SEQ ID NO 78
<211> LENGTH: 23
<212> TYPE: PRT
<213> ORGANISM: Artificial Sequence
<220> FEATURE:
<223> OTHER INFORMATION: synthesized

<400> SEQUENCE: 78

Leu Ser Ala Lys Glu Ala Cys Ala Arg Glu Lys Ala Ala Arg Glu Ala
1               5                   10                  15

Ala Cys Arg Ala Gly Gly Lys
            20

<210> SEQ ID NO 79
<211> LENGTH: 23
<212> TYPE: PRT
<213> ORGANISM: Artificial Sequence
<220> FEATURE:
<223> OTHER INFORMATION: synthesized

<400> SEQUENCE: 79

Leu Ser His Ala Glu Ala Cys Ala Arg Glu His Ala Ala Arg Glu Ala
1               5                   10                  15

Ala Cys Arg Ala Gly Gly Lys
            20

<210> SEQ ID NO 80
<211> LENGTH: 23
<212> TYPE: PRT
<213> ORGANISM: Artificial Sequence
<220> FEATURE:
<223> OTHER INFORMATION: synthesized

<400> SEQUENCE: 80

Leu Ser Arg Ala Glu Ala Cys Ala Arg Glu His Ala Ala Arg Glu Ala
1               5                   10                  15

Ala Cys Arg Ala Gly Gly Lys
            20

<210> SEQ ID NO 81
<211> LENGTH: 23
<212> TYPE: PRT
<213> ORGANISM: Artificial Sequence
<220> FEATURE:
<223> OTHER INFORMATION: synthesized
```

```
<400> SEQUENCE: 81

Leu Ser Lys Ala Glu Ala Cys Ala Arg Glu His Ala Ala Arg Glu Ala
1               5                   10                  15

Ala Cys Arg Ala Gly Gly Lys
            20

<210> SEQ ID NO 82
<211> LENGTH: 23
<212> TYPE: PRT
<213> ORGANISM: Artificial Sequence
<220> FEATURE:
<223> OTHER INFORMATION: synthesized

<400> SEQUENCE: 82

Leu Ser His Ala Glu Ala Cys Ala Arg Glu Arg Ala Ala Arg Glu Ala
1               5                   10                  15

Ala Cys Arg Ala Gly Gly Lys
            20

<210> SEQ ID NO 83
<211> LENGTH: 23
<212> TYPE: PRT
<213> ORGANISM: Artificial Sequence
<220> FEATURE:
<223> OTHER INFORMATION: synthesized

<400> SEQUENCE: 83

Leu Ser Arg Ala Glu Ala Cys Ala Arg Glu Arg Ala Ala Arg Glu Ala
1               5                   10                  15

Ala Cys Arg Ala Gly Gly Lys
            20

<210> SEQ ID NO 84
<211> LENGTH: 23
<212> TYPE: PRT
<213> ORGANISM: Artificial Sequence
<220> FEATURE:
<223> OTHER INFORMATION: synthesized

<400> SEQUENCE: 84

Leu Ser Lys Ala Glu Ala Cys Ala Arg Glu Arg Ala Ala Arg Glu Ala
1               5                   10                  15

Ala Cys Arg Ala Gly Gly Lys
            20

<210> SEQ ID NO 85
<211> LENGTH: 23
<212> TYPE: PRT
<213> ORGANISM: Artificial Sequence
<220> FEATURE:
<223> OTHER INFORMATION: synthesized

<400> SEQUENCE: 85

Leu Ser His Ala Glu Ala Cys Ala Arg Glu Lys Ala Ala Arg Glu Ala
1               5                   10                  15

Ala Cys Arg Ala Gly Gly Lys
            20

<210> SEQ ID NO 86
<211> LENGTH: 23
<212> TYPE: PRT
<213> ORGANISM: Artificial Sequence
<220> FEATURE:
<223> OTHER INFORMATION: synthesized
```

```
<400> SEQUENCE: 86

Leu Ser Arg Ala Glu Ala Cys Ala Arg Glu Lys Ala Ala Arg Glu Ala
1               5                   10                  15

Ala Cys Arg Ala Gly Gly Lys
            20

<210> SEQ ID NO 87
<211> LENGTH: 23
<212> TYPE: PRT
<213> ORGANISM: Artificial Sequence
<220> FEATURE:
<223> OTHER INFORMATION: synthesized

<400> SEQUENCE: 87

Leu Ser Lys Ala Glu Ala Cys Ala Arg Glu Lys Ala Ala Arg Glu Ala
1               5                   10                  15

Ala Cys Arg Ala Gly Gly Lys
            20

<210> SEQ ID NO 88
<211> LENGTH: 23
<212> TYPE: PRT
<213> ORGANISM: Artificial Sequence
<220> FEATURE:
<223> OTHER INFORMATION: synthesized

<400> SEQUENCE: 88

Leu Ser His His Glu Ala Cys Ala Arg Glu His Ala Ala Arg Glu Ala
1               5                   10                  15

Ala Cys Arg Ala Gly Gly Lys
            20

<210> SEQ ID NO 89
<211> LENGTH: 23
<212> TYPE: PRT
<213> ORGANISM: Artificial Sequence
<220> FEATURE:
<223> OTHER INFORMATION: synthesized

<400> SEQUENCE: 89

Leu Ser His Arg Glu Ala Cys Ala Arg Glu His Ala Ala Arg Glu Ala
1               5                   10                  15

Ala Cys Arg Ala Gly Gly Lys
            20

<210> SEQ ID NO 90
<211> LENGTH: 23
<212> TYPE: PRT
<213> ORGANISM: Artificial Sequence
<220> FEATURE:
<223> OTHER INFORMATION: synthesized

<400> SEQUENCE: 90

Leu Ser His Lys Glu Ala Cys Ala Arg Glu His Ala Ala Arg Glu Ala
1               5                   10                  15

Ala Cys Arg Ala Gly Gly Lys
            20

<210> SEQ ID NO 91
<211> LENGTH: 23
<212> TYPE: PRT
<213> ORGANISM: Artificial Sequence
<220> FEATURE:
<223> OTHER INFORMATION: synthesized
```

```
<400> SEQUENCE: 91

Leu Ser His His Glu Ala Cys Ala Arg Glu Arg Ala Ala Arg Glu Ala
1               5                   10                  15

Ala Cys Arg Ala Gly Gly Lys
            20

<210> SEQ ID NO 92
<211> LENGTH: 23
<212> TYPE: PRT
<213> ORGANISM: Artificial Sequence
<220> FEATURE:
<223> OTHER INFORMATION: synthesized

<400> SEQUENCE: 92

Leu Ser His Arg Glu Ala Cys Ala Arg Glu Arg Ala Ala Arg Glu Ala
1               5                   10                  15

Ala Cys Arg Ala Gly Gly Lys
            20

<210> SEQ ID NO 93
<211> LENGTH: 23
<212> TYPE: PRT
<213> ORGANISM: Artificial Sequence
<220> FEATURE:
<223> OTHER INFORMATION: synthesized

<400> SEQUENCE: 93

Leu Ser His Lys Glu Ala Cys Ala Arg Glu Arg Ala Ala Arg Glu Ala
1               5                   10                  15

Ala Cys Arg Ala Gly Gly Lys
            20

<210> SEQ ID NO 94
<211> LENGTH: 23
<212> TYPE: PRT
<213> ORGANISM: Artificial Sequence
<220> FEATURE:
<223> OTHER INFORMATION: synthesized

<400> SEQUENCE: 94

Leu Ser His His Glu Ala Cys Ala Arg Glu Lys Ala Ala Arg Glu Ala
1               5                   10                  15

Ala Cys Arg Ala Gly Gly Lys
            20

<210> SEQ ID NO 95
<211> LENGTH: 23
<212> TYPE: PRT
<213> ORGANISM: Artificial Sequence
<220> FEATURE:
<223> OTHER INFORMATION: synthesized

<400> SEQUENCE: 95

Leu Ser His Arg Glu Ala Cys Ala Arg Glu Lys Ala Ala Arg Glu Ala
1               5                   10                  15

Ala Cys Arg Ala Gly Gly Lys
            20

<210> SEQ ID NO 96
<211> LENGTH: 23
<212> TYPE: PRT
<213> ORGANISM: Artificial Sequence
<220> FEATURE:
<223> OTHER INFORMATION: synthesized
```

```
<400> SEQUENCE: 96

Leu Ser His Lys Glu Ala Cys Ala Arg Glu Lys Ala Ala Arg Glu Ala
1               5                   10                  15

Ala Cys Arg Ala Gly Gly Lys
            20

<210> SEQ ID NO 97
<211> LENGTH: 23
<212> TYPE: PRT
<213> ORGANISM: Artificial Sequence
<220> FEATURE:
<223> OTHER INFORMATION: synthesized

<400> SEQUENCE: 97

Leu Ser Arg His Glu Ala Cys Ala Arg Glu His Ala Ala Arg Glu Ala
1               5                   10                  15

Ala Cys Arg Ala Gly Gly Lys
            20

<210> SEQ ID NO 98
<211> LENGTH: 23
<212> TYPE: PRT
<213> ORGANISM: Artificial Sequence
<220> FEATURE:
<223> OTHER INFORMATION: synthesized

<400> SEQUENCE: 98

Leu Ser Arg Arg Glu Ala Cys Ala Arg Glu His Ala Ala Arg Glu Ala
1               5                   10                  15

Ala Cys Arg Ala Gly Gly Lys
            20

<210> SEQ ID NO 99
<211> LENGTH: 23
<212> TYPE: PRT
<213> ORGANISM: Artificial Sequence
<220> FEATURE:
<223> OTHER INFORMATION: synthesized

<400> SEQUENCE: 99

Leu Ser Arg Lys Glu Ala Cys Ala Arg Glu His Ala Ala Arg Glu Ala
1               5                   10                  15

Ala Cys Arg Ala Gly Gly Lys
            20

<210> SEQ ID NO 100
<211> LENGTH: 23
<212> TYPE: PRT
<213> ORGANISM: Artificial Sequence
<220> FEATURE:
<223> OTHER INFORMATION: synthesized

<400> SEQUENCE: 100

Leu Ser Arg His Glu Ala Cys Ala Arg Glu Arg Ala Ala Arg Glu Ala
1               5                   10                  15

Ala Cys Arg Ala Gly Gly Lys
            20

<210> SEQ ID NO 101
<211> LENGTH: 23
<212> TYPE: PRT
<213> ORGANISM: Artificial Sequence
<220> FEATURE:
<223> OTHER INFORMATION: synthesized
```

-continued

```
<400> SEQUENCE: 101

Leu Ser Arg Arg Glu Ala Cys Ala Arg Glu Arg Ala Ala Arg Glu Ala
1               5                   10                  15

Ala Cys Arg Ala Gly Gly Lys
            20

<210> SEQ ID NO 102
<211> LENGTH: 23
<212> TYPE: PRT
<213> ORGANISM: Artificial Sequence
<220> FEATURE:
<223> OTHER INFORMATION: synthesized

<400> SEQUENCE: 102

Leu Ser Arg Lys Glu Ala Cys Ala Arg Glu Arg Ala Ala Arg Glu Ala
1               5                   10                  15

Ala Cys Arg Ala Gly Gly Lys
            20

<210> SEQ ID NO 103
<211> LENGTH: 23
<212> TYPE: PRT
<213> ORGANISM: Artificial Sequence
<220> FEATURE:
<223> OTHER INFORMATION: synthesized

<400> SEQUENCE: 103

Leu Ser Arg His Glu Ala Cys Ala Arg Glu Lys Ala Ala Arg Glu Ala
1               5                   10                  15

Ala Cys Arg Ala Gly Gly Lys
            20

<210> SEQ ID NO 104
<211> LENGTH: 23
<212> TYPE: PRT
<213> ORGANISM: Artificial Sequence
<220> FEATURE:
<223> OTHER INFORMATION: synthesized

<400> SEQUENCE: 104

Leu Ser Arg Arg Glu Ala Cys Ala Arg Glu Lys Ala Ala Arg Glu Ala
1               5                   10                  15

Ala Cys Arg Ala Gly Gly Lys
            20

<210> SEQ ID NO 105
<211> LENGTH: 23
<212> TYPE: PRT
<213> ORGANISM: Artificial Sequence
<220> FEATURE:
<223> OTHER INFORMATION: synthesized

<400> SEQUENCE: 105

Leu Ser Arg Lys Glu Ala Cys Ala Arg Glu Lys Ala Ala Arg Glu Ala
1               5                   10                  15

Ala Cys Arg Ala Gly Gly Lys
            20

<210> SEQ ID NO 106
<211> LENGTH: 23
<212> TYPE: PRT
<213> ORGANISM: Artificial Sequence
<220> FEATURE:
<223> OTHER INFORMATION: synthesized
```

```
<400> SEQUENCE: 106

Leu Ser Lys His Glu Ala Cys Ala Arg Glu His Ala Ala Arg Glu Ala
1               5                   10                  15

Ala Cys Arg Ala Gly Gly Lys
            20

<210> SEQ ID NO 107
<211> LENGTH: 23
<212> TYPE: PRT
<213> ORGANISM: Artificial Sequence
<220> FEATURE:
<223> OTHER INFORMATION: synthesized

<400> SEQUENCE: 107

Leu Ser Lys Arg Glu Ala Cys Ala Arg Glu His Ala Ala Arg Glu Ala
1               5                   10                  15

Ala Cys Arg Ala Gly Gly Lys
            20

<210> SEQ ID NO 108
<211> LENGTH: 23
<212> TYPE: PRT
<213> ORGANISM: Artificial Sequence
<220> FEATURE:
<223> OTHER INFORMATION: synthesized

<400> SEQUENCE: 108

Leu Ser Lys Lys Glu Ala Cys Ala Arg Glu His Ala Ala Arg Glu Ala
1               5                   10                  15

Ala Cys Arg Ala Gly Gly Lys
            20

<210> SEQ ID NO 109
<211> LENGTH: 23
<212> TYPE: PRT
<213> ORGANISM: Artificial Sequence
<220> FEATURE:
<223> OTHER INFORMATION: synthesized

<400> SEQUENCE: 109

Leu Ser Lys His Glu Ala Cys Ala Arg Glu Arg Ala Ala Arg Glu Ala
1               5                   10                  15

Ala Cys Arg Ala Gly Gly Lys
            20

<210> SEQ ID NO 110
<211> LENGTH: 23
<212> TYPE: PRT
<213> ORGANISM: Artificial Sequence
<220> FEATURE:
<223> OTHER INFORMATION: synthesized

<400> SEQUENCE: 110

Leu Ser Lys Arg Glu Ala Cys Ala Arg Glu Arg Ala Ala Arg Glu Ala
1               5                   10                  15

Ala Cys Arg Ala Gly Gly Lys
            20

<210> SEQ ID NO 111
<211> LENGTH: 23
<212> TYPE: PRT
<213> ORGANISM: Artificial Sequence
<220> FEATURE:
<223> OTHER INFORMATION: synthesized
```

```
<400> SEQUENCE: 111

Leu Ser Lys Lys Glu Ala Cys Ala Arg Glu Arg Ala Ala Arg Glu Ala
1               5                   10                  15

Ala Cys Arg Ala Gly Gly Lys
            20

<210> SEQ ID NO 112
<211> LENGTH: 23
<212> TYPE: PRT
<213> ORGANISM: Artificial Sequence
<220> FEATURE:
<223> OTHER INFORMATION: synthesized

<400> SEQUENCE: 112

Leu Ser Lys His Glu Ala Cys Ala Arg Glu Lys Ala Ala Arg Glu Ala
1               5                   10                  15

Ala Cys Arg Ala Gly Gly Lys
            20

<210> SEQ ID NO 113
<211> LENGTH: 23
<212> TYPE: PRT
<213> ORGANISM: Artificial Sequence
<220> FEATURE:
<223> OTHER INFORMATION: synthesized

<400> SEQUENCE: 113

Leu Ser Lys Arg Glu Ala Cys Ala Arg Glu Lys Ala Ala Arg Glu Ala
1               5                   10                  15

Ala Cys Arg Ala Gly Gly Lys
            20

<210> SEQ ID NO 114
<211> LENGTH: 23
<212> TYPE: PRT
<213> ORGANISM: Artificial Sequence
<220> FEATURE:
<223> OTHER INFORMATION: synthesized

<400> SEQUENCE: 114

Leu Ser Lys Lys Glu Ala Cys Ala Arg Glu Lys Ala Ala Arg Glu Ala
1               5                   10                  15

Ala Cys Arg Ala Gly Gly Lys
            20
```